US012653406B2

(12) United States Patent
Honma et al.

(10) Patent No.: US 12,653,406 B2
(45) Date of Patent: Jun. 16, 2026

(54) COMPUTER PROGRAM, INFORMATION PROCESSING METHOD, INFORMATION PROCESSING DEVICE, AND INFORMATION PROCESSING SYSTEM

(71) Applicant: TERUMO KABUSHIKI KAISHA, Tokyo (JP)

(72) Inventors: Yasuyuki Honma, Ashigarakamigun Matsudamachi (JP); Takayuki Uchida, Hiratsuka (JP); Yuta Yoshida, Sagamihara (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 288 days.

(21) Appl. No.: 18/354,698

(22) Filed: Jul. 19, 2023

(65) Prior Publication Data

US 2023/0355120 A1     Nov. 9, 2023

Related U.S. Application Data

(63) Continuation of application No. PCT/JP2022/010172, filed on Mar. 9, 2022.

(30) Foreign Application Priority Data

Mar. 16, 2021     (JP) ................................. 2021-042842

(51) Int. Cl.
*A61B 5/024* (2006.01)

(52) U.S. Cl.
CPC ...... *A61B 5/02405* (2013.01); *A61B 5/02416* (2013.01)

(58) Field of Classification Search
None
See application file for complete search history.

(56) References Cited

U.S. PATENT DOCUMENTS 7,468,034 B2     12/2008     Ouchi
2010/0204550 A1*     8/2010     Heneghan ................ A61B 5/08
600/529

(Continued)

FOREIGN PATENT DOCUMENTS

JP     2000083927 A     *     3/2000
JP     2005270570 A     10/2005

(Continued)

OTHER PUBLICATIONS

Kebe et al., "Human Vital Signs Detection Methods and Potential Using Radars: A Review", Sensors 2020, 20, 1454. (Year: 2020).*

(Continued)

*Primary Examiner* — Yi-Shan Yang
(74) *Attorney, Agent, or Firm* — .Buchanan Ingersoll & Rooney PC

(57) ABSTRACT

An information processing method for determining an abnormality in a heart or a blood vessel of a living body, and the method includes: specifying a displacement site at which a surface of the living body is displaced due to the heart or the blood vessel and that is detectable from a first direction; specifying a displacement site at which the surface of the living body is displaced due to the heart or the blood vessel and that is detectable from a second direction; detecting a pulse of the heart or the blood vessel based on the displacement of the surface of the living body at each of the specified displacement sites; and determining an abnormality in the heart or the blood vessel based on information related to the detected pulse of the heart or the blood vessel.

18 Claims, 18 Drawing Sheets

(56)        References Cited

U.S. PATENT DOCUMENTS

| | | | |
|---|---|---|---|
| 2018/0085067 A1 | 3/2018 | Sato | |
| 2020/0039382 A1 | 2/2020 | Ozawa et al. | |
| 2020/0187837 A1 | 6/2020 | Leabman | |
| 2020/0321104 A1 * | 10/2020 | Lindström | ............. G16H 40/67 |

FOREIGN PATENT DOCUMENTS

| | | | |
|---|---|---|---|
| JP | 2016174872 A | | 10/2016 |
| JP | 2019180451 A | | 10/2019 |
| JP | 2019201698 A | * | 11/2019 |

OTHER PUBLICATIONS

English Translations of the International Search Report (Form PCT/ISA/210) and the Written Opinion of the International Searching Authority (Form PCT/ISA/237) issued May 31, 2022, by the Japan Patent Office in corresponding International Application No. PCT/JP2022/010172. (7 pages).
International Search Report (PCT/ISA/210) with translation and Written Opinion (PCT/ISA/237) mailed on May 31, 2022, by the Japanese Patent Office as the International Searching Authority for International Application No. PCT/JP2022/010172. (9 pages).
The extended European Search Report issued Nov. 20, 2023, by the European Patent Office in corresponding European Patent Application No. 22771223.9-1113. (9 pages).

* cited by examiner

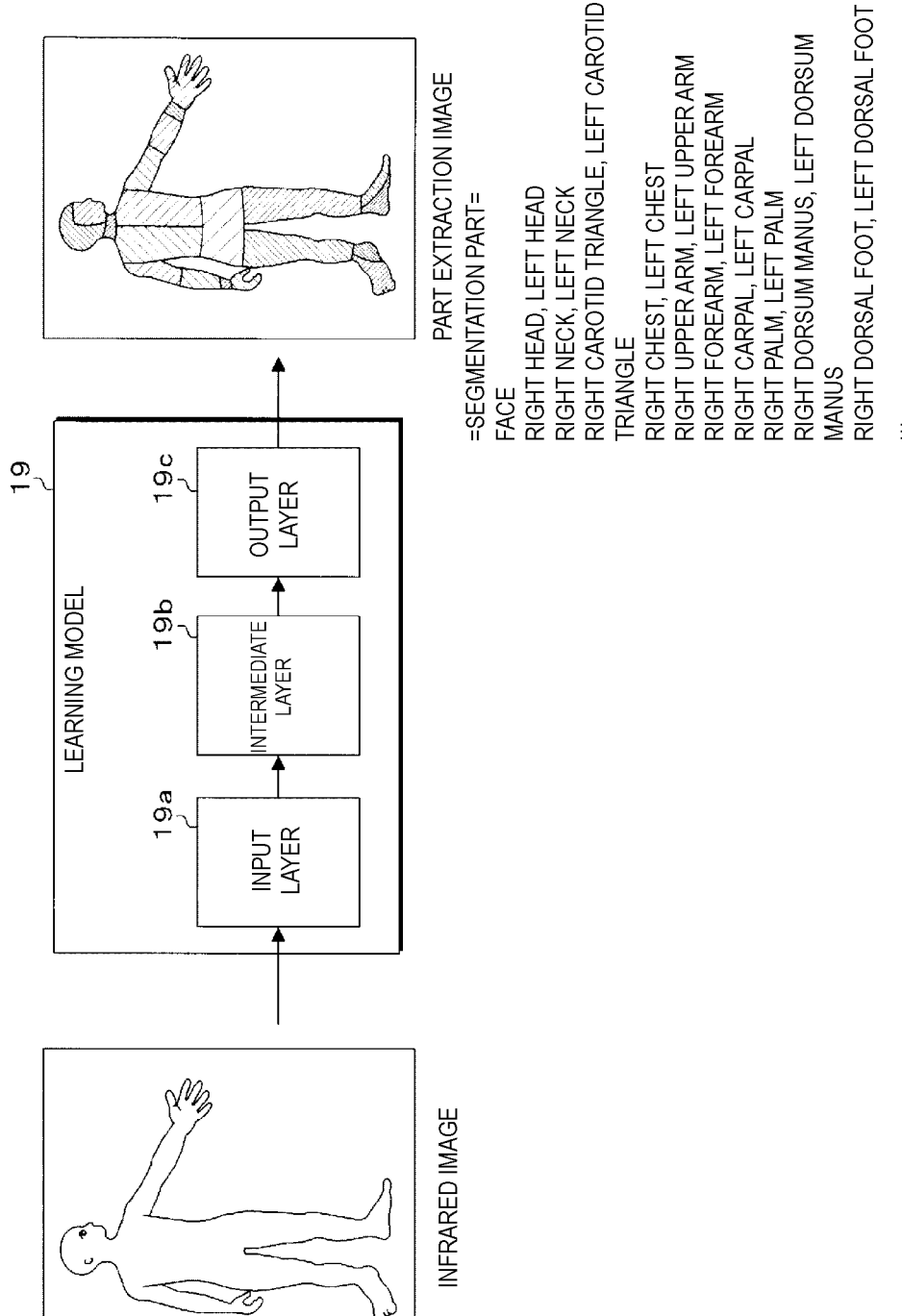

FIG. 3

INFRARED IMAGE

LEARNING MODEL 19

INPUT LAYER 19a

INTERMEDIATE LAYER 19b

OUTPUT LAYER 19c

PART EXTRACTION IMAGE

SEGMENTATION PART=

PART EXTRACTION PART=
FACE
RIGHT HEAD, LEFT HEAD
RIGHT NECK, LEFT NECK
RIGHT CAROTID TRIANGLE, LEFT CAROTID TRIANGLE
RIGHT CHEST, LEFT CHEST
RIGHT UPPER ARM, LEFT UPPER ARM
RIGHT FOREARM, LEFT FOREARM
RIGHT CARPAL, LEFT CARPAL
RIGHT PALM, LEFT PALM
RIGHT DORSUM MANUS, LEFT DORSUM MANUS
RIGHT DORSAL FOOT, LEFT DORSAL FOOT
...

TEMPORAL REGION OF HEAD (TEMPORAL ARTERY)

NECK (CAROTID ARTERY)

UPPER ARM (BRACHIAL ARTERY)

PORTION CLOSE TO THUMB ON INSIDE OF CARPAL (RADIAL ARTERY)

PORTION CLOSE TO LITTLE FINGER ON INSIDE OF CARPAL (ULNAR ARTERY)

CHEST (HEART)

DORSAL FOOT (DORSALIS PEDIS ARTERY)

COMPUTER PROGRAM, INFORMATION PROCESSING METHOD, INFORMATION PROCESSING DEVICE, AND INFORMATION PROCESSING SYSTEM

CROSS-REFERENCES TO RELATED APPLICATIONS

This application is a continuation of International Application No. PCT/JP2022/010172 filed on Mar. 9, 2022, which claims priority to Japanese Application No. 2021-042842 filed on Mar. 16, 2021, the entire content of both of which is incorporated herein by reference.

TECHNOLOGICAL FIELD

The present disclosure generally relates to a computer program, an information processing method, an information processing device, and an information processing system.

BACKGROUND DISCUSSION

Japanese Patent Application Publication No. 2005-270570 A describes a living body information monitoring device that monitors living body information such as a pulse by emitting high-frequency electromagnetic waves, detecting reflected waves scattered by a surface of a living body of a person, and calculating a temporal change of the surface of the living body.

However, Japanese Patent Application Publication No. 2005-270570 A does not describe a technique for determining a specific abnormality in a heart or a blood vessel.

SUMMARY

A computer program, an information processing method, an information processing device, and an information processing system are disclosed that can detect a pulse of a heart or a blood vessel of a living body and determine an abnormality in the heart or the blood vessel.

A non-transitory computer-readable medium storing a computer program according to the present aspect is a computer program causing a computer to determine an abnormality in a heart or a blood vessel of a living body by executing processes including: specifying a displacement site at which a surface of the living body is displaced due to the heart or the blood vessel and that is detectable from a first direction; specifying a displacement site at which the surface of the living body is displaced due to the heart or the blood vessel and that is detectable from a second direction; detecting a pulse of the heart or the blood vessel based on the displacement of the surface of the living body at each of the specified displacement sites; and determining an abnormality in the heart or the blood vessel based on information related to the detected pulse of the heart or the blood vessel.

In accordance with an aspect, the non-transitory computer-readable medium further executes a process comprising: specifying a plurality of the displacement sites, and determining an abnormality in the heart or the blood vessel by comparing a pulse rate, a pulse rhythm, or a magnitude of a fluctuation of the pulse among the plurality of specified displacement sites.

In accordance with another aspect, the non-transitory computer-readable medium further executes a process comprising: specifying a plurality of the displacement sites, and determining that there is an abnormality in the heart or the blood vessel when a time difference between a peak of the pulse at a first one of the displacement sites and a peak of the pulse at a second one of the displacement sites is equal to or greater than a threshold.

In accordance with a further aspect, the non-transitory computer-readable medium further executes a process comprising: specifying the displacement sites based on signal data output from a non-contact sensor.

In accordance with an aspect, the non-transitory computer-readable medium further executes a process comprising: specifying the displacement sites by infrared rays or visible light, and emitting millimeter waves or electromagnetic waves in a terahertz band and detecting the pulse of the heart or the blood vessel based on reflected waves from each of the displacement sites of the living body.

In accordance with another aspect, the non-transitory computer-readable medium further executes a process comprising: specifying the displacement site based on signal data output from a first infrared sensor or visible light sensor facing the first direction with respect to the living body, and specifying the displacement site based on signal data output from a second infrared sensor or visible light sensor facing the second direction with respect to the living body.

In accordance with a further aspect, the non-transitory computer-readable medium further executes a process comprising: specifying each of the displacement sites based on signal data output from a first infrared sensor or visible light sensor facing the first direction with respect to the living body and signal data output from a second infrared sensor or visible light sensor facing the second direction with respect to the living body.

In accordance with an aspect, the non-transitory computer-readable medium further executes a process comprising: detecting the pulse of the heart or the blood vessel based on signal data output from a first millimeter wave sensor or terahertz band sensor that emits millimeter waves or electromagnetic waves in a terahertz band to the living body in the first direction and receives reflected waves from the displacement site of the living body, and detecting the pulse of the heart or the blood vessel based on signal data output from a second millimeter wave sensor or terahertz band sensor that emits millimeter waves or electromagnetic waves in a terahertz band to the living body in the second direction and receives reflected waves from the displacement site of the living body.

In accordance with another aspect, the first direction is a substantially horizontal direction, and the second direction is a substantially vertical direction.

In accordance with a further aspect, the non-transitory computer-readable medium further executes a process comprising: emitting millimeter waves or electromagnetic waves in a terahertz band while aiming at the specified displacement sites, and detecting the pulse of the heart or the blood vessel based on reflected waves from each of the displacement sites.

In accordance with an aspect, the non-transitory computer-readable medium further executes a process comprising: detecting the pulse of the heart or the blood vessel at one or more of the displacement sites based on signal data output from a contact sensor attached to the living body, and detecting the pulse of the heart or the blood vessel at one or more of the displacement sites based on signal data output from a non-contact sensor.

In accordance with another aspect, the non-transitory computer-readable medium further executes a process comprising: determining whether a magnitude of body motion is less than a predetermined value based on signal data output from an acceleration sensor attached to the living body, and detecting the pulse of the heart or the blood vessel based on the displacement of the surface of the living body at each of the specified displacement sites when the magnitude of body motion is less than the predetermined value.

In accordance with a further aspect, the displacement sites are a neck, a temporal region of a head, an upper limb, a dorsal foot, or a chest, and the non-transitory computer-readable medium can further execute a process comprising: detecting a carotid artery in the neck, a superficial temporal artery in the temporal region of the head, a brachial artery, a radial artery or an ulnar artery in the upper limb, a dorsalis pedis artery in the dorsal foot, or a heartbeat of the heart in the chest.

In accordance with an aspect, the non-transitory computer-readable medium further executes a process comprising: specifying a region of a carotid triangle as the displacement site, and detecting a pulse of the carotid artery.

In accordance with another aspect, the non-transitory computer-readable medium further executes a process comprising: detecting any one of a contour, an eye, an eyebrow, a nose, a mouth, a nasolabial fold, an ear, and a chin of a face, specifying the displacement site in which the carotid artery is present based on a deviation amount of the detected part from a median line, and detecting a pulse of the carotid artery.

In accordance with a further aspect, the non-transitory computer-readable medium further executes a process comprising: specifying an upper arm as the displacement site, and detecting a pulse of the brachial artery.

In accordance with an aspect, the non-transitory computer-readable medium further executes a process comprising: specifying a portion close to a thumb on an inside of a carpal as the displacement site, and detecting a pulse of the radial artery.

In accordance with another aspect, the non-transitory computer-readable medium further executes a process comprising: specifying a portion close to a little finger on an inside of the carpal as the displacement site, and detecting a pulse of the ulnar artery.

In accordance with a further aspect, the non-transitory computer-readable medium further executes a process comprising: determining an abnormality in the heart or the blood vessel based on any two of a pulse of the carotid artery, a pulse of the superficial temporal artery, a pulse of the brachial artery, a pulse of the radial artery, a pulse of the ulnar artery, a pulse of the dorsalis pedis artery, and a heartbeat.

In accordance with an aspect, the non-transitory computer-readable medium further executes a process comprising: determining an abnormality in the heart or the blood vessel based on a pulse of the carotid artery, a pulse of the superficial temporal artery, a pulse of the brachial artery, a pulse of the radial artery, a pulse of the ulnar artery, or a pulse of the dorsalis pedis artery, and a heartbeat.

In accordance with another aspect, the non-transitory computer-readable medium further executes a process comprising: determining an abnormality in the heart or the blood vessel based on a deviation in peak of a pulse of the carotid artery, a pulse of the superficial temporal artery, a pulse of the brachial artery, a pulse of the radial artery, a pulse of the ulnar artery, or a pulse of the dorsalis pedis artery.

In accordance with a further aspect, the non-transitory computer-readable medium further executes a process comprising: determining an abnormality related to critical limb ischemia based on a magnitude of a fluctuation of a pulse in the dorsalis pedis artery.

In accordance with an aspect, the non-transitory computer-readable medium further executes a process comprising: determining an abnormality of the heart or the blood vessel based on a pulse of a left carotid artery and a pulse of a right carotid artery.

In accordance with another aspect, the non-transitory computer-readable medium further executes a process comprising: determining an abnormality in the heart or the blood vessel based on a pulse of a left temporal artery and a pulse of a right temporal artery.

In accordance with a further aspect, the non-transitory computer-readable medium further executes a process comprising: determining an abnormality in the heart or the blood vessel based on a pulse of a left brachial artery and a pulse of a right brachial artery.

In accordance with an aspect, the non-transitory computer-readable medium further executes a process comprising: determining an abnormality in the heart or the blood vessel based on a pulse of a left dorsalis pedis artery and a pulse of a right dorsalis pedis artery.

In accordance with another aspect, the non-transitory computer-readable medium further executes a process comprising: specifying a region of a carotid triangle as the displacement site, detecting jugular venous distension, and determining an abnormality related to heart failure.

An information processing method according to the present aspect is an information processing method for determining an abnormality in a heart or a blood vessel of a living body, and the method includes: specifying a displacement site at which a surface of the living body is displaced due to the heart or the blood vessel and that is detectable from a first direction; specifying a displacement site at which the surface of the living body is displaced due to the heart or the blood vessel and that is detectable from a second direction; detecting a pulse of the heart or the blood vessel based on the displacement of the surface of the living body at each of the specified displacement sites; and determining an abnormality in the heart or the blood vessel based on information related to the detected pulse of the heart or the blood vessel.

An information processing device according to the present aspect is an information processing device for determining an abnormality in a heart or a blood vessel of a living body, and the information processing device includes: a first specifying unit configured to specify a displacement site at which a surface of the living body is displaced due to the heart or the blood vessel and that is detectable from a first direction; a second specifying unit configured to specify a displacement site at which the surface of the living body is displaced due to the heart or the blood vessel and that is detectable from a second direction; a detection unit configured to detect a pulse of the heart or the blood vessel based on the displacement of the surface of the living body at each of the specified displacement sites specified by the first specifying unit and the second specifying unit; and a determination unit configured to determine an abnormality in the heart or the blood vessel based on information related to the detected pulse of the heart or the blood vessel.

An information processing system according to the present aspect is an information processing system including an information processing device and a sensor device for determining an abnormality in a heart or a blood vessel of a living body. The information processing device includes a first infrared sensor or visible light sensor configured to specify, from a first direction, a displacement site at which a surface of the living body is displaced due to the heart or the blood vessel, and a first millimeter wave sensor or terahertz band sensor configured to emit millimeter waves or electromagnetic waves in a terahertz band to the living body in the first direction and receive reflected waves from the displacement site of the living body. The sensor device includes a second infrared sensor or visible light sensor configured to specify, from a second direction, a displacement site at which the surface of the living body is displaced due to the heart or the blood vessel, and a second millimeter wave sensor or terahertz band sensor configured to emit millimeter waves or electromagnetic waves in a terahertz band to the living body in the second direction and receive reflected waves from the displacement site of the living body. The information processing system includes: a specifying unit configured to specify the displacement sites respectively based on signal data output from the first infrared sensor or visible light sensor and the second infrared sensor or visible light sensor, a detection unit configured to emit millimeter waves or electromagnetic waves in a terahertz band to the displacement sites specified by the specifying unit from the first millimeter wave sensor or terahertz band sensor and the second millimeter wave sensor or terahertz band sensor, and to detect a pulse of the heart or the blood vessel based on the signal data output from the first millimeter wave sensor or terahertz band sensor and the second millimeter wave sensor or terahertz band sensor, and a determination unit configured to determine an abnormality in the heart or the blood vessel based on information related to the detected pulse of the heart or the blood vessel.

According to the above, a computer program, an information processing method, an information processing device, and an information processing system that can detect a pulse of a heart or a blood vessel of a living body and determine an abnormality in the heart or the blood vessel can be provided.

BRIEF DESCRIPTION OF THE DRAWINGS

FIG. 3 is a conceptual diagram illustrating an example of a learning model according to Embodiment 1.

DETAILED DESCRIPTION

Specific examples of a computer program, an information processing method, an information processing device, and an information processing system according to embodiments of the invention will be described below with reference to the drawings. The disclosure is not limited to these examples, is defined by the claims, and is intended to include all modifications within meanings and scopes equivalent to that of the claims. In addition, at least a part of the embodiments to be described below may be combined freely.

Embodiment 1

Figure 1:
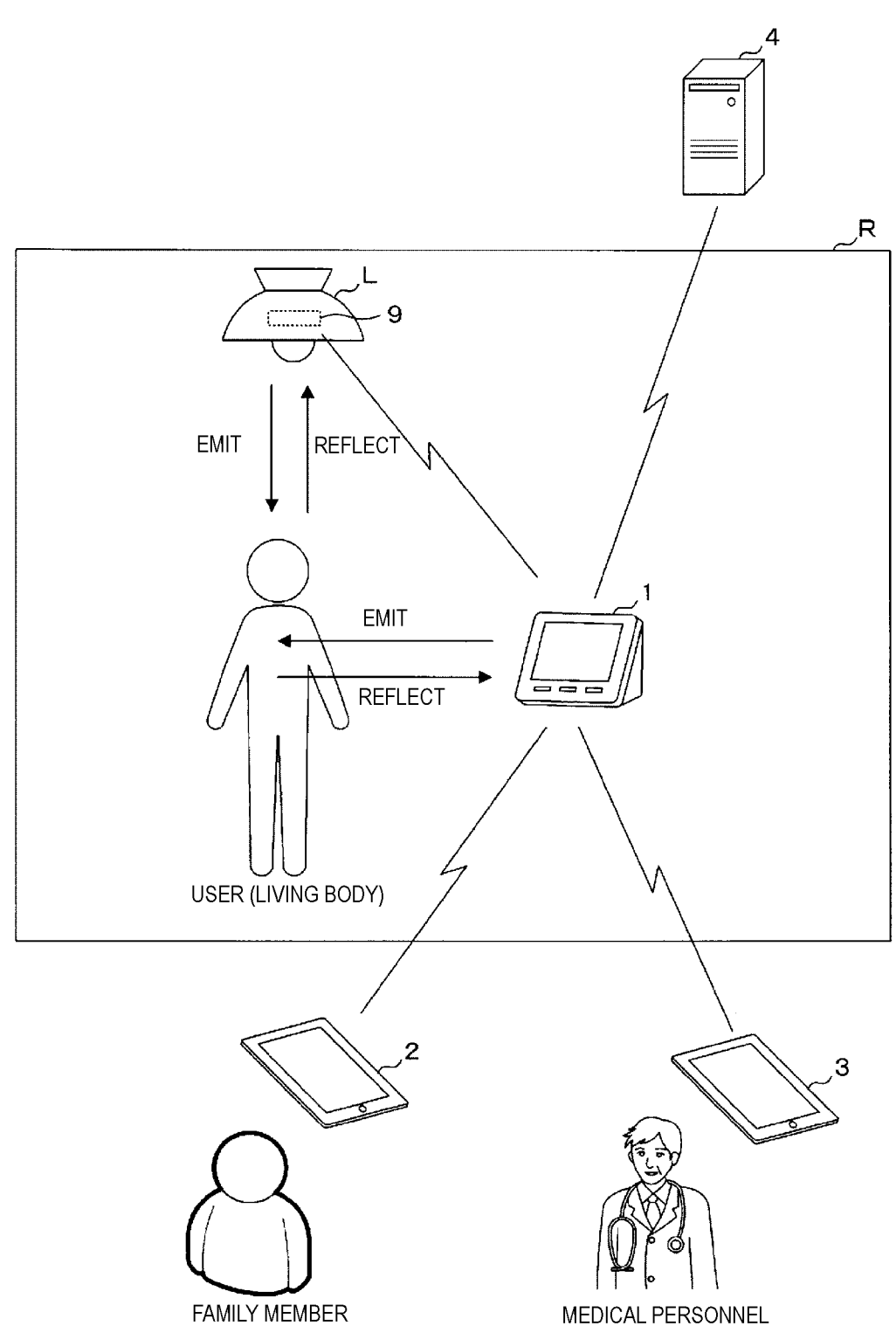
FIG. 1 is a diagram illustrating a configuration example of an information processing system according to Embodiment 1.

FIG. 1 is a diagram illustrating a configuration example of an information processing system according to Embodiment 1. The information processing system includes an information processing device 1 and a sensor device 9 according to Embodiment 1. The information processing device 1 can be wirelessly connected to the sensor device 9, a first communication terminal 2, a second communication terminal 3, and a server 4, and can transmit and receive various kinds of information.

The information processing device 1 is a device that detects a pulse of a heart and a blood vessel of a user (living body) by using infrared rays and millimeter waves, and determines whether there is an abnormality in the heart and the blood vessel. The information processing device 1 can be, for example, installed in a room R of the user. The sensor device 9 is a device that detects the pulse of the heart and the blood vessel of the user (living body) in the same manner as the information processing device 1, and transmits a detection result to the information processing device 1. The sensor device 9 can be provided, for example, in a lighting device L installed on a ceiling of the room R. The first communication terminal 2 is a communication device used, for example, by a family member of the user. The second communication terminal 3 is a communication terminal used, for example, by a medical personnel. The server 4 is a device that provides information related to an environment that affects heartbeats of the user, such as a temperature and a humidity. Each device may be connected, for example, by a wired cable.

The abnormality in the heart in the present embodiment refers to a disease of the heart itself. The abnormality in the blood vessel can include an abnormality in the blood vessel itself such as arteriosclerosis, and an abnormality in an organ and a site due to an abnormality in blood flow, such as cerebral infarction and leg infarction (critical limb ischemia).

Figure 2:
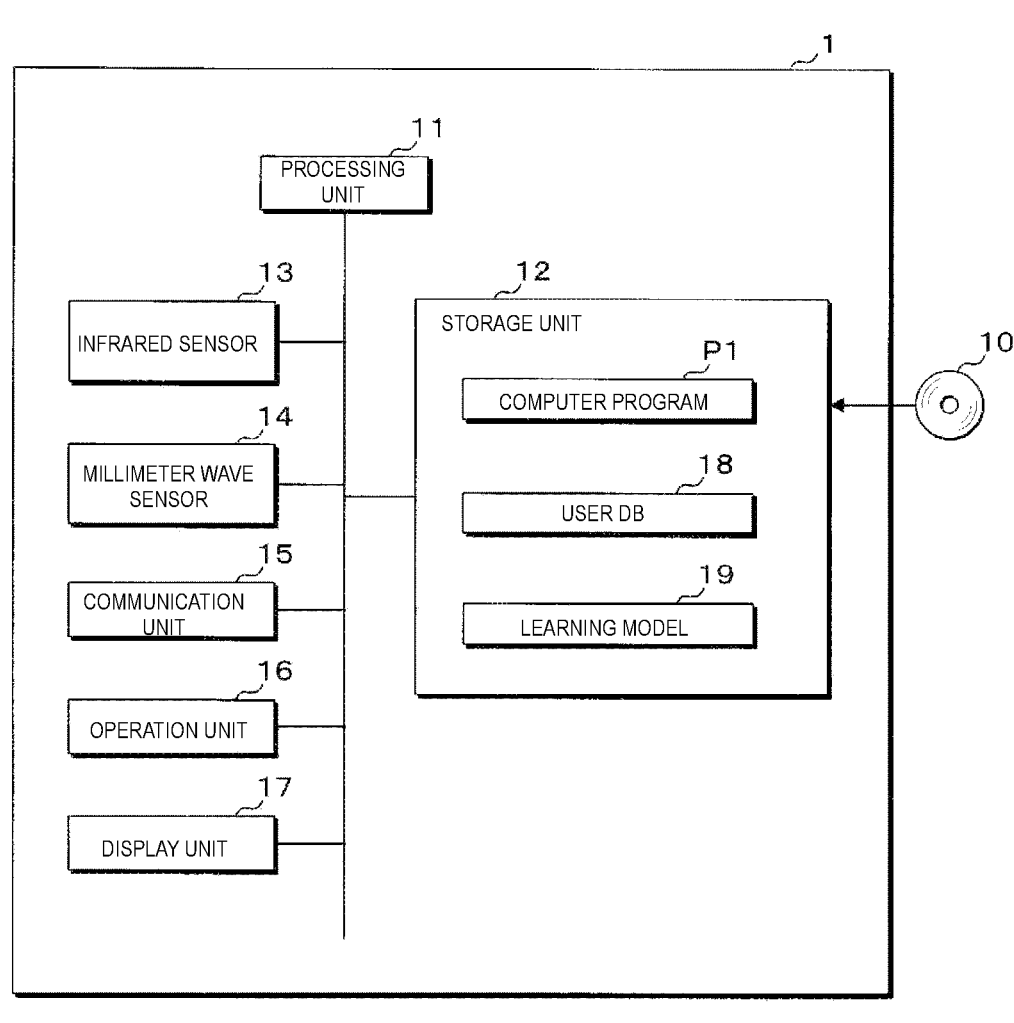
FIG. 2 is a block diagram illustrating a configuration example of an information processing device according to Embodiment 1.

FIG. 2 is a block diagram illustrating a configuration example of the information processing device 1 according to Embodiment 1. The information processing device 1 is a computer including a processing unit 11, a storage unit 12, an infrared sensor 13, a millimeter wave sensor 14, a communication unit 15, an operation unit 16, and a display unit 17. The information processing device 1 may be a multi-computer including a plurality of computers, or may be a virtual machine virtually constructed by software.

The processing unit 11 is an arithmetic processing device including one or more central processing units (CPUs), micro-processing units (MPUs), graphics processing units (GPUs), general-purpose computing on graphics processing units (GPGPUs), tensor processing units (TPUs), or the like. The processing unit 11 reads and executes a computer program P1 stored in the storage unit 12, thereby executing processing of determining the abnormality in the heart and the blood vessels of the user.

The storage unit 12 is a storage device such as a hard disk, an electrically erasable programmable read-only memory (ROM) (EEPROM), or a flash memory. The storage unit 12 stores the computer program P1 for causing the processing unit 11 to execute processing of causing the computer to determine the abnormality in the heart and the blood vessels of the user, a user database (DB) 18, and a learning model 19.

The computer program P1 is a program for causing the computer to function as the information processing device 1 according to Embodiment 1 and executing an information processing method according to Embodiment 1. The computer program P1 causes the computer to execute processing of specifying displacement sites at each of which a surface of the living body is displaced due to the heart or the blood vessel of the user, detecting a pulse of the heart or the blood vessel based on the displacements of the surface of the living body at the specified displacement sites, and determining an abnormality of the heart or the blood vessel based on information related to the detected pulse of the heart or blood vessel.

The computer program P1 may be recorded in a recording medium 10 in a computer-readable manner. The storage unit 12 stores the computer program P1 read from the recording medium 10 by a reading device. The recording medium 10 can be, for example, a semiconductor memory such as a flash memory, an optical disk, a magnetic disk; a magneto-optical disk, or the like. In addition, the computer program P1 according to the present embodiment may be downloaded from a program providing server connected to a communication network, and stored in the storage unit 12.

The user DB 18 can store identification information for identifying the user, authentication information for authenticating each individual user, and basic information of the user such as name, sex, and age. In addition, the user DB 18 stores pulses and heartbeats of the user and a detection date and time which are detected by the information processing device 1, and environmental information such as a temperature and a humidity in association with the identification information of the user. Further, the user DB 18 can store a determination result obtained by the information processing device 1, that is, information indicating whether the heart or the blood vessel of the user is normal, in association with the identification information of the user. The user DB 18 may be, for example, a cloud database.

The infrared sensor 13 can be, for example, an infrared laser such as light detection and ranging (LiDAR), or an infrared camera, and is a sensor for specifying, in a non-contact manner, each part of a human body of the user and the displacement sites at each of which the surface of the living body is displaced due to the pulse of the heart or the blood vessel by using infrared rays. The infrared sensor 13 is an example of a non-contact sensor for specifying the displacement sites on the surface of the living body from a first direction. The first direction can be, for example, a substantially horizontal direction. That is, the infrared sensor

13 is a sensor for identifying the displacement sites of the user from a substantially horizontal direction. The infrared sensor 13 has a high spatial resolution and is suitable for capturing a structure of an object. However, there is a disadvantage that a displacement of the surface of the living body, which is likely to be absorbed by clothing or the like and is hidden by the clothing, cannot be captured.

The substantially horizontal direction is not a strictly horizontal direction, and may be a direction oblique to a vertical direction and a horizontal plane as long as being a direction in which a part on a front side of a standing user can be detected.

The infrared camera is a camera including a lens and a complementary metal-oxide semiconductor (CMOS) image sensor for receiving infrared rays reflected by the surface of the living body or the clothing of the user, and outputs infrared image data (signal data) as two-dimensional information of the user. The infrared image data is image data including a plurality of pixels arranged in the substantially horizontal direction and the vertical direction.

The infrared sensor 13, which is a LiDAR, includes a light emitting element that emits infrared rays to the user, and a light receiving element that receives the infrared rays that are emitted and then reflected by the user. The light emitting element can be, for example, an infrared laser such as a vertical cavity surface emitting laser (VCSEL), and emits dot patterns arranged vertically and horizontally to the user. The light receiving element can be, for example, a CMOS image sensor. The infrared sensor 13 calculates a distance to the user based on a round-trip time from when the infrared rays are emitted to the user up to when the infrared rays are reflected back. The infrared sensor 13 calculates distances to each dot pattern, and outputs point group data (signal data) which is three-dimensional information of the user. The point group data can represent, for example, a large number of points on a surface of a living body or a surface of the clothing of the user by three-dimensional coordinates. The processing unit 11 can convert the point group data into voxel data. In addition, the processing unit 11 can convert the point group data or the voxel data into two-dimensional infrared image data.

Hereinafter, in order to simplify the description, an example for specifying each part of the body of the user which is the user, and the displacement sites at which the surface of the living body is displaced due to the pulse of the heart and the blood vessels by using the two-dimensional infrared image data will be described.

The millimeter wave sensor 14 is a sensor for detecting the pulse at each of the displacement sites of the user by using millimeter waves. Although the millimeter wave sensor 14 is inferior to the infrared sensor 13 in spatial resolution, since electromagnetic waves of millimeter waves are transmitted without being absorbed by the clothing of the user and are reflected by the surface of the living body, the millimeter wave sensor 14 is suitable for capturing the displacement of the surface of the living body. In particular, the millimeter wave sensor 14 emits the millimeter waves from the first direction to the user, and receives reflected waves from each of the displacement sites of the user, thereby detecting the pulse at each of the displacement sites. The first direction is the substantially horizontal direction. That is, the millimeter wave sensor 14 emits the millimeter waves in the substantially horizontal direction toward the user, and receives the reflected waves from each of the displacement sites of the user, thereby detecting the pulse at each of the displacement sites.

The millimeter wave sensor 14 includes a synthesizer that generates a millimeter wave signal, a transmitting antenna, a receiving antenna, a mixer, and the like. The transmitting antenna transmits electromagnetic waves of millimeter waves generated by the synthesizer. The receiving antenna receives electromagnetic waves of the millimeter waves reflected by the surface of the living body of the user. The mixer is a circuit that mixes the transmitting waves and the receiving waves to generate an intermediate frequency signal. The processing unit 11 can calculate the distance to the user based on data of the intermediate frequency signal. In particular, the processing unit 11 can calculate variation in the distance to the displacement site of the user, that is, the displacement of the surface of the living body, and can detect the pulse of the heart or the blood vessel at the displacement site. The millimeter wave sensor 14 can emit the millimeter waves while aiming at displacement site by an electronic scan method, and the processing unit 11 can detect the pulse at the displacement sites.

The communication unit 15 includes a processing circuit for performing wireless communication processing, a communication circuit, and the like, and transmits and receives various kinds of information to and from the sensor device 9, the first communication terminal 2, the second communication terminal 3, and the server 4 via a router.

The operation unit 16 is an input device that receives an operation of the information processing device 1 from the user. The input device can be, for example, a pointing device such as a touch panel, or a keyboard.

The display unit 17 is an output device that outputs a determination result for an abnormality of the heart or the blood vessel of the user. The output device can be, for example, a liquid crystal display or an electroluminescent (EL) display.

FIG. 3 is a conceptual diagram illustrating an example of the learning model 19 according to Embodiment 1. The learning model 19 is a model for recognizing a predetermined object included in an infrared image. For example, the learning model 19 can classify the object in units of pixels by using an image recognition technique using semantic segmentation, and can recognize, as an object, each part of a human body included in the infrared image. Specifically, the learning model 19 can recognize, for example, in units of pixels, a face, a right temporal region of the head, a left temporal region of the head, a right neck, a left neck, a right carotid triangle, a left carotid triangle, a right chest, a left chest, a right upper arm, a left upper arm, a right forearm, a left forearm, a right carpal, a left carpal, a right palm, a left palm, a right dorsum manus, a left dorsum manus, a right dorsal foot, a left dorsal foot, and the like of the human body in the infrared image. The upper arm, the forearm, the carpal, the palm, and the dorsum manus constitute an upper limb.

The learning model 19 can be, for example, a convolutional neural network (CNN) trained by deep learning. The learning model 19 includes an input layer 19a for receiving the infrared image data, an intermediate layer 19b for extracting and restoring a feature of the infrared image, and an output layer 19c for outputting part extraction image data indicating the object included in the infrared image in units of pixels. The learning model 19 can be, for example, U-Net.

The input layer 19a of the learning model 19 includes a plurality of neurons for receiving input of the infrared image data, that is, pixel values of the pixels constituting the infrared image, and transmit the input pixel values to the intermediate layer 19b. The intermediate layer 19b includes a convolutional layer (CONV layer) and a deconvolution layer (DECONV layer). The convolutional layer is a layer that dimensionally compresses the infrared image data. The feature of the object is extracted by the dimensional compression. The deconvolution layer performs deconvolution processing and restores an original dimension. By the restoration processing in the deconvolution layer, the part extraction image data in which each pixel has a pixel value (class data) corresponding to a class of the object is generated. The output layer 19c includes a plurality of neurons that output the part extraction image data. A part extraction image is an image in which classification, for example, color coding, is performed for each part of the human body.

The learning model 19 can be generated by preparing training data including the infrared image data obtained by the infrared sensor 13 and the part extraction image data obtained by adding the class data corresponding to a type of a corresponding part of the human body to each pixel of the infrared image, and causing an untrained neural network to perform machine learning using the training data.

According to the learning model 19 trained in this way, the part extraction image data in which each part of the human body is classified in units of pixels is obtained by inputting the infrared image data, which is obtained by the infrared sensor 13 from the human body, to the learning model 19 as illustrated in FIG. 3.

In the above example, the example in which each part of the human body in the infrared image, which is two-dimensional information, is recognized has been described, and each part of the human body in the three-dimensional point group data obtained by the LiDAR or in the voxel data may be recognized. For example, the processing unit 11 can convert the point group data into the voxel data, generate a plurality of pieces of two-dimensional image data based on the voxel data, perform image recognition processing on each piece of two-dimensional image data in the same manner as described above, and inversely transform two-dimensional part extraction image data into the voxel data or the point group data in a plurality of images, thereby obtaining data indicating the type of each part of the human body in the three-dimensional data in units of voxels or point data.

In addition, the type of each part of the human body may be recognized by using the learning model 19 such as a 3D U-Net that can directly recognize each part of the user in the voxel data. Further, each part of the human body in the three-dimensional information may be recognized by using a machine learning method.

The processing unit 11 can recognize each part of the human body of the user in the infrared image by using the learning model 19. On the surface of the living body, there are displacement sites at each of which the pulse of the heart or the blood vessel is specifically propagated and appears as periodic displacement of the surface of the living body. The processing unit 11 specifies the displacement sites based on a recognition result using the learning model 19.

Figure 4:
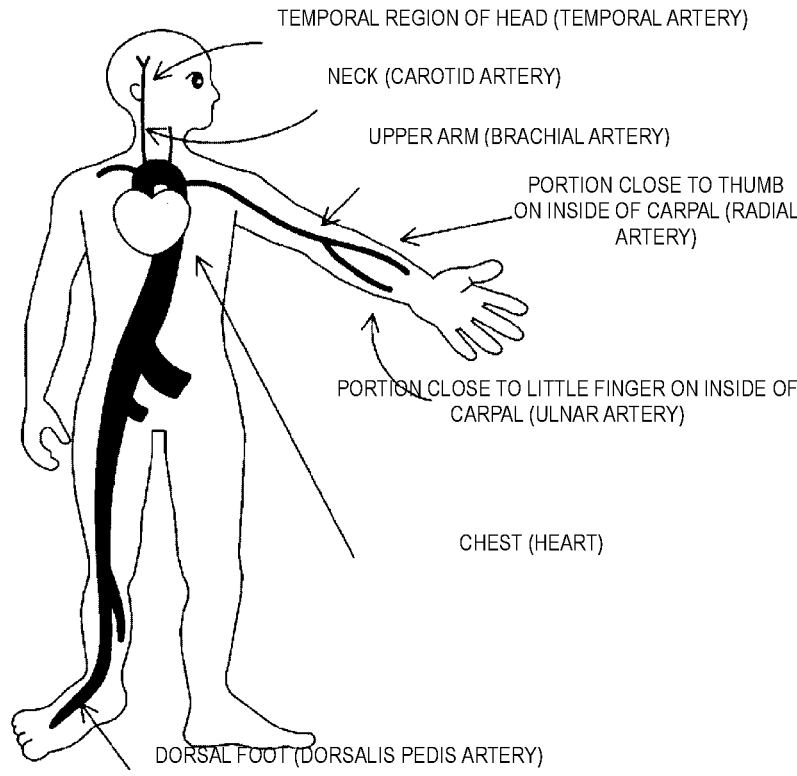
FIG. 4 is a conceptual diagram illustrating displacement sites, a heart, and blood vessels.

FIG. 4 is a conceptual diagram illustrating displacement sites, the heart, and the blood vessels. The displacement sites can be, for example, the neck, the temporal region of the head, the upper arm, a portion close to a thumb on an inside of the carpal, a portion close to a little finger on the inside of the carpal, the dorsal foot, and the chest. A carotid artery is present in the neck, a superficial temporal artery is present in the temporal region of the head, a brachial artery is present in the upper arm, a radial artery is present in the portion close to a thumb on an inside of the carpal, an ulnar artery is present in the portion close to a little finger on the inside of the carpal, dorsalis pedis artery is present in the dorsal foot, and the heart is present in the chest.

Figure 5:
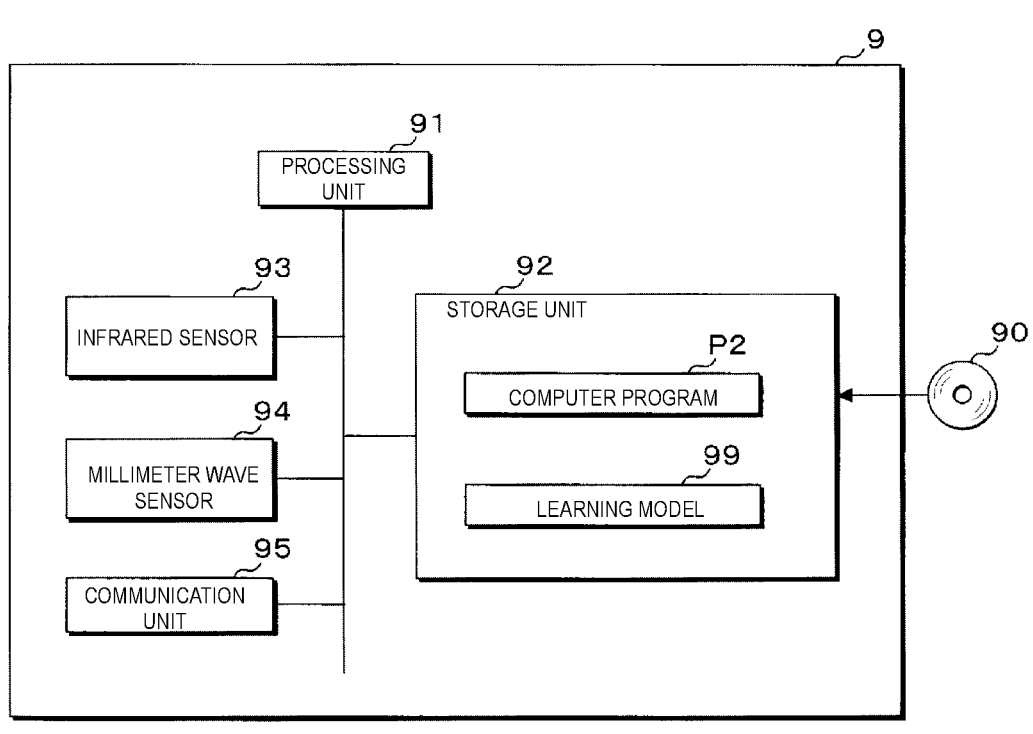
FIG. 5 is a block diagram illustrating a configuration example of a sensor device according to Embodiment 1.

FIG. 5 is a block diagram illustrating a configuration example of the sensor device 9 according to Embodiment 1. The sensor device 9 is a computer including a processing unit 91, a storage unit 92, an infrared sensor 93, a millimeter wave sensor 94, and a communication unit 95 similar to those of the information processing device 1.

The processing unit 91 is an arithmetic processing unit including one or more central processing units (CPUs), graphics processing units (GPUs), general-purpose computing on graphics processing units (GPGPUs), tensor processing units (TPUs), and the like. The processing unit 91 reads and executes a computer program P2 stored in the storage unit 92, thereby executing the processing of detecting the pulses of the heart and the blood vessels of the user.

The storage unit 92 is a storage device such as a hard disk, an electrically erasable programmable read-only memory (EEPROM), or a flash memory. The storage unit 92 stores the computer program P2 for causing the processing unit 91 to execute processing for causing the computer to perform processing for detecting the pulses of the heart and the blood vessels of the user, and a learning model 99. A structure of the learning model 99 is the same as that of the learning model 19. However, the learning model 99 may be trained such that each part of the human body can be recognized from the infrared image of the user captured from above. For example, the learning model 99 may recognize a head, an ear, or a shoulder as viewed from above in addition to the parts that can be recognized by the learning model 19.

The computer program P2 is a program for causing the computer to function as the sensor device 9 according to Embodiment 1. The computer program P2 causes the computer to execute processing of specifying the displacement sites at each of which the surface of the living body is displaced due to the heart or the blood vessel of the user and detecting the pulses of the heart or the blood vessel based on the displacement of the surface of the living body at each of the specified displacement sites.

The computer program P2 may be recorded in a recording medium 90 in a computer-readable manner. The storage unit 92 stores the computer program P2 read from the recording medium 90 by a reading device. The recording medium 90 is a semiconductor memory such as a flash memory, an optical disk, a magnetic disk, a magneto-optical disk, or the like. In addition, the computer program P2 according to the present embodiment may be downloaded from a program providing server connected to a communication network, and stored in the storage unit 92.

The infrared sensor 93 can be, for example, an infrared laser such as LiDAR, or an infrared camera, and is a sensor for specifying, in a non-contact manner, each part of the human body of the user and the displacement sites at each of which the surface of the living body is displaced due to the pulse of the heart or the blood vessel from a second direction by using infrared rays. The second direction can be, for example, a substantially vertical direction. That is, the infrared sensor 93 is a sensor for specifying the displacement sites of the user from above. The infrared sensor 93 is an example of a non-contact sensor for specifying the displacement sites on the surface of the living body, and the infrared sensor 93 has the same structure as the infrared sensor 13.

The substantially vertical direction is not a strictly vertical direction, and may be a direction oblique to the vertical direction and the horizontal plane as long as being a direction in which a part of the standing user can be detected from a top side of the head.

The millimeter wave sensor 94 is a sensor for detecting the pulse at each of the displacement sites of the user by using millimeter waves (i.e., electromagnetic waves). A structure of the millimeter wave sensor 94 is the same as that of the millimeter wave sensor 14. In particular, the millimeter wave sensor 94 emits the millimeter waves from the second direction to the user, and receives reflected waves from each of the displacement sites of the user, thereby detecting the pulse at each of the displacement sites. The second direction is a substantially vertical direction. That is, the millimeter wave sensor 94 emits the millimeter waves forward the user from above to below, and receives the reflected waves from each of the displacement sites of the user, thereby detecting the pulse at each of the displacement sites.

The communication unit 95 includes a processing circuit for performing wireless communication processing, a communication circuit, and the like, and transmits and receives various kinds of information to and from the information processing device 1 via a router.

Figure 6:
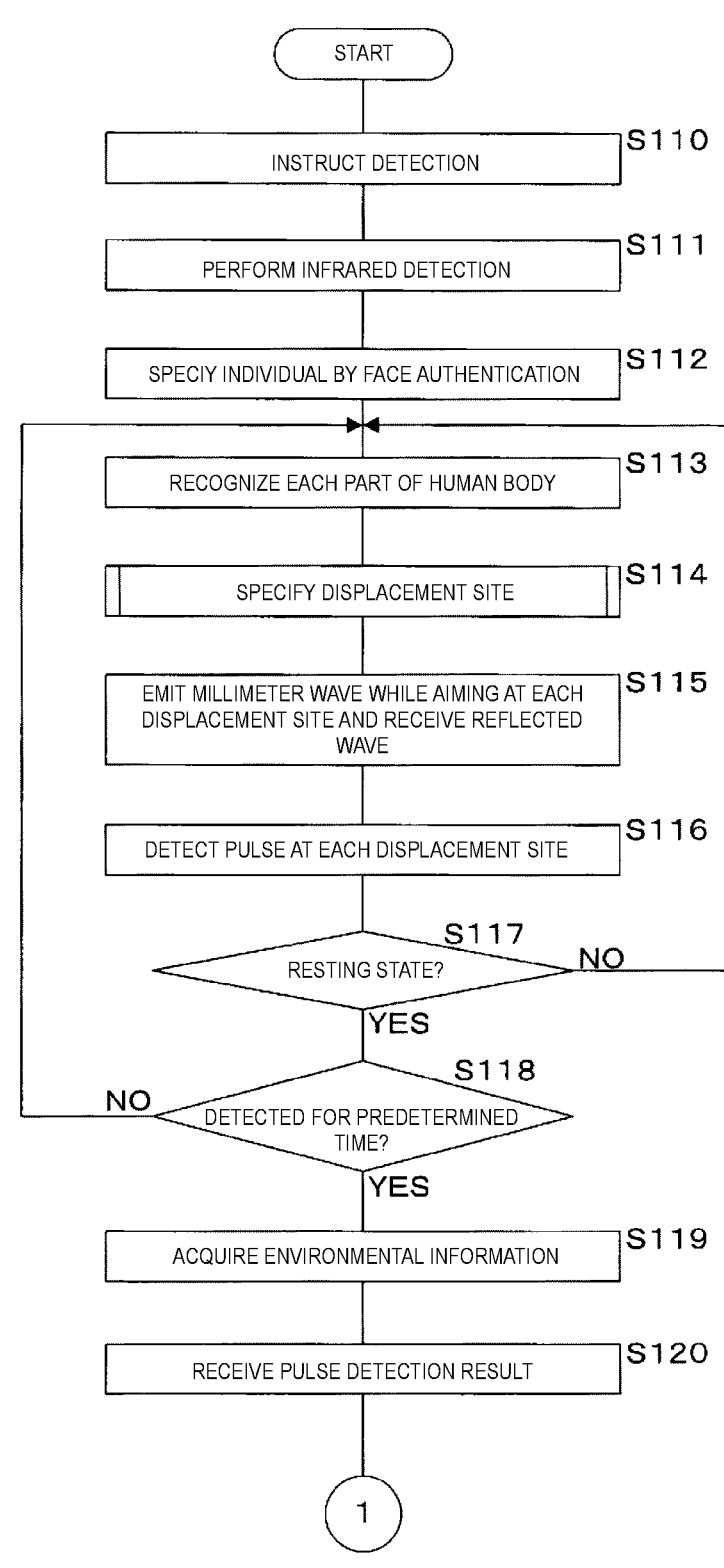
FIG. 6 is a flowchart illustrating an information processing procedure according to Embodiment 1.
Figure 7:
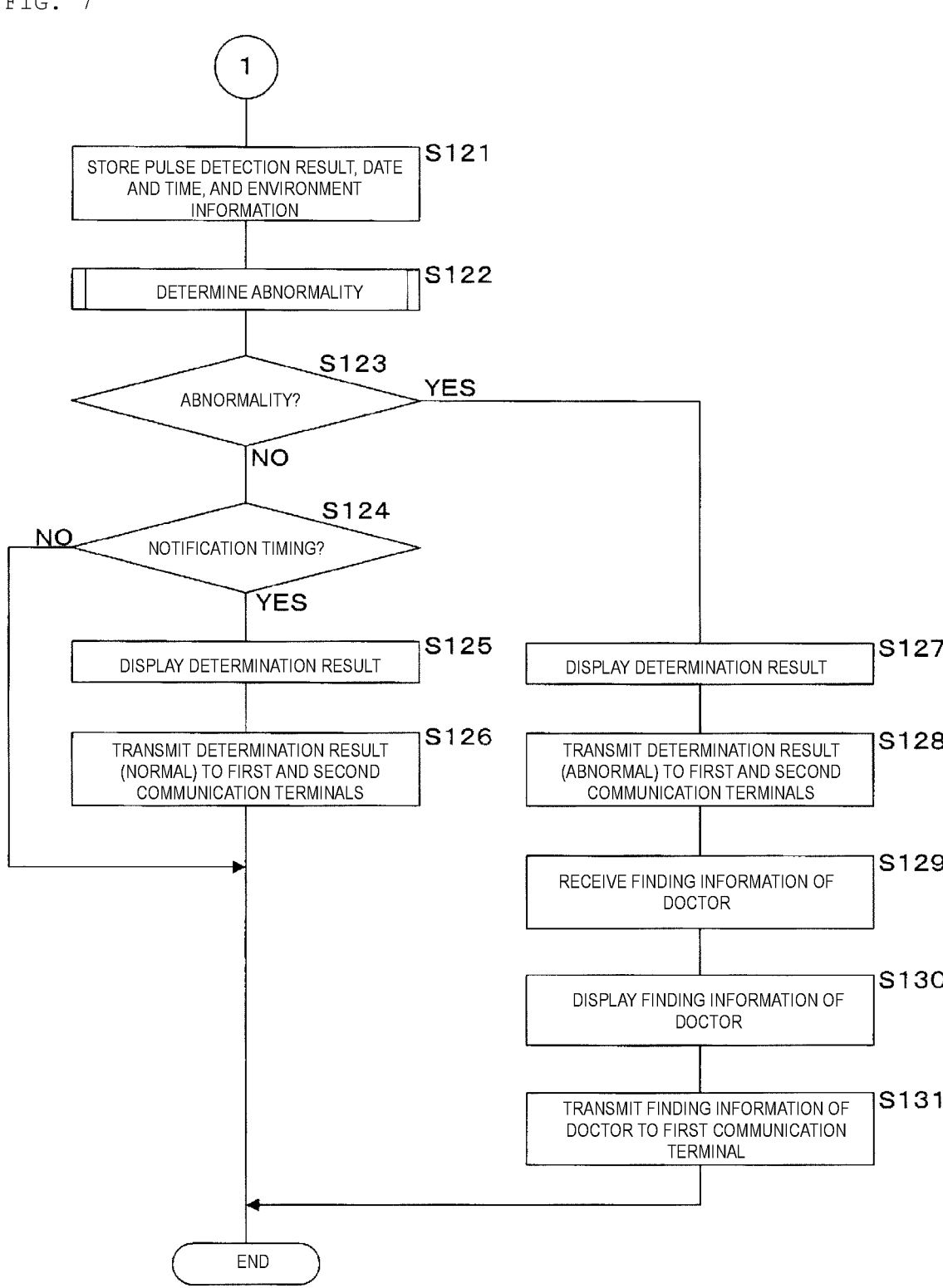
FIG. 7 is a flowchart illustrating the information processing procedure according to Embodiment 1.

FIGS. 6 and 7 are flowcharts illustrating an information processing procedure according to Embodiment 1. The information processing device 1 periodically executes the following processing at any timing, for example, three times every day. The processing unit 11 transmits, to the sensor device 9, an instruction signal to instruct the processing including specifying the displacement sites of the user and detecting the pulse (S110). That is, the processing unit 11 detects the displacement site and the pulse of the user captured from above, and requests the sensor device 9 to transmit information of a pulse detection result indicating the pulse at the detected displacement site. Details of the processing performed by the sensor device 9 will be described later.

The processing unit 11 performs infrared detection on the user by using the infrared sensor 13 (S111). Specifically, when the infrared sensor 13 is an infrared camera, the processing unit 11 images the user by using the infrared camera and acquires the infrared image data of the user. When the infrared sensor 13 is a LiDAR, the processing unit 11 acquires the point group data of the user by using the LiDAR. The processing unit 11 converts the point group data into the two-dimensional infrared image data.

Next, the processing unit 11 specifies an individual by face authentication processing using a result of the infrared detection (S112). For example, the processing unit 11 extracts a predetermined feature from the infrared image data or the point group data of the user, and specifies the user individual by collating the extracted feature with the authentication information registered in the user DB 18.

Next, the processing unit 11 inputs the infrared image data to the learning model 19 to recognize each part of the human body of the user in the infrared image (S113). Then, the processing unit 11 specifies displacement sites at each of which the surface of the living body is periodically displaced due to the pulse of the heart or the blood vessel (S114). Details of the processing of specifying the displacement sites will be described later. The processing unit 11 that executes the processing in S114 functions as a first specifying unit that specifies the displacement sites at each of which the surface of the living body is displaced due to the heart or the blood vessel.

Next, based on a specification result in S114, the processing unit 11 sequentially emits millimeter waves while aiming at each specified displacement site, receives reflected waves (S115), and detects the pulse of the heart or blood vessel at each displacement site (S116).

For example, the processing unit 11 detects a temporal change of the pulse, a pulse rate, a heartbeat, a pulse rhythm, a magnitude of a fluctuation of the pulse, or a peak time point of the pulse. The temporal change of the pulse can be, in other words, a temporal change in a displacement amount of the surface of the living body at the displacement site. The pulse rate can be, for example, the number of pulse per minute of an artery. The heartbeat can be, for example, the number of pulse per minute of the heart. The pulse rhythm can be, for example, a pulse period or a numerical value indicating regularity of the pulse period at the displacement site. The magnitude of the fluctuation of the pulse is an amplitude of the displacement of the surface of the living body at the displacement site. The peak time point of the pulse is a time at which the displacement amount at the displacement site is maximum. A time point at which the displacement amount is minimum may be detected.

The processing unit 11 that executes the processing in S115 to S116 functions as a detection unit that detects the pulse of the heart or the blood vessel based on the displacement of the surface of the living body at the specified displacement site.

Next, the processing unit 11 determines whether the user is in a resting state based on a period of the detected pulse (S117). For example, the processing unit 11 reads information related to past pulse (i.e., number of heart beats per minute) of the individual specified by the face authentication from the user DB 18 and compares a currently detected pulse period with a past pulse period, thereby determining whether the user is in the resting state. When the current pulse period is extremely shorter than the past pulse period (i.e., a higher heartbeat), it may be determined that the user is not in the resting state (for example, a state that is not during or immediately after exercise including relaxing, sitting, lying down, and sleeping).

When it is determined that the user is not in the resting state (S117: NO), the processing unit 11 returns the processing to S113. When it is determined that the user is in the resting state (S117: YES), the processing unit 11 determines whether the pulse of each displacement site is detected for a predetermined time (S118). The predetermined time can be, for example, a time that is several times an average pulse period of the heart and the blood vessel. When it is determined that the pulse is detected for a time shorter than the predetermined time (S118: NO), the processing unit 11 returns the processing to S113. When it is determined that the pulse is detected for a predetermined time or longer than the predetermined time (S118: YES), the processing unit 11 accesses the server 4 and acquires the environmental information such as a current temperature and humidity (S119).

The processing unit 11 receives the information of the pulse detection result transmitted from the sensor device 9 (S120).

Next, the processing unit 11 stores, in the user DB 18, the pulse detection result indicating the pulse at each displacement site, a date and time when the pulse was detected, and the environment information acquired in S119 in association with the identification information of the user (S121). The pulse detection result includes a pulse detection result detected by the information processing device 1 and a pulse detection result detected by the sensor device 9.

Next, the processing unit 11 determines an abnormality in the heart or the blood vessel based on the pulse detection result at each of the plurality of specified displacement sites (S122). Specifically, the abnormality of the heart or the blood vessel is determined by comparing the temporal change of the pulse, the pulse rate, the heartbeat, the pulse rhythm, the magnitude of the fluctuation of the pulse, the peak time point of the pulse, and the like at each of the plurality of specified displacement sites. Details of the abnormality determination processing will be described later. The processing unit 11 that executes the processing in S122 functions as a determination unit that determines the abnormality of the heart or the blood vessel based on the information related to the detected pulse of the heart or blood vessel.

The processing unit 11 determines whether there is an abnormality in the heart or the blood vessel (S123). When it is determined that there is no abnormality (S123: NO), the processing unit 11 determines whether a current time is a predetermined notification timing (S124). Since it is considered that, when there is no abnormality, display of the determination result and the notification to the related person do not need to be performed each time the abnormality determination is performed, the determination of the notification timing is performed in S124. The display and the notification may be performed each time the determination processing is performed.

When it is determined that the current time is not the notification timing (S124: NO), the processing ends. When it is determined that the current time is the notification timing (S124: YES), the processing unit 11 generates a determination result display image 171 (see FIG. 12) indicating that there is no abnormality, and displays the determination result display image 171 on the display unit 17 (S125). Then, the processing unit 11 transmits the determination result to the first communication terminal 2 of the family member and the second communication terminal 3 of the medical personnel (S126). The processing unit 11 may transmit the determination result to the first communication terminal 2 and the second communication terminal 3 together with information such as the name, the identification information, and a contact address of the user. Personal information, for example, such as the name of the user may not be transmitted to the second communication terminal 3 of the medical personnel.

When it is determined in S123 that there is an abnormality (S123: YES), the processing unit 11 generates the determination result display image 171 (see FIGS. 13 and 14) indicating that there is an abnormality, and displays the determination result display image 171 on the display unit 17 (S127). Then, the processing unit 11 transmits the determination result to the first communication terminal 2 of the family member and the second communication terminal 3 of the medical personnel (S128).

The medical personnel can receive information of the determination result by the second communication terminal 3, and transmits finding information indicating findings on the determination result to the information processing device 1.

The processing unit 11 of the information processing device 1 receives, via the communication unit 15, the finding information transmitted from the second communication terminal 3 of the medical personnel (S129), and displays the received finding information of the medical personnel on the display unit 17 (S130). In addition, the processing unit 11 transmits the finding information of the medical personnel to the first communication terminal 2 of the family member (S131), and ends the processing.

Figure 8:
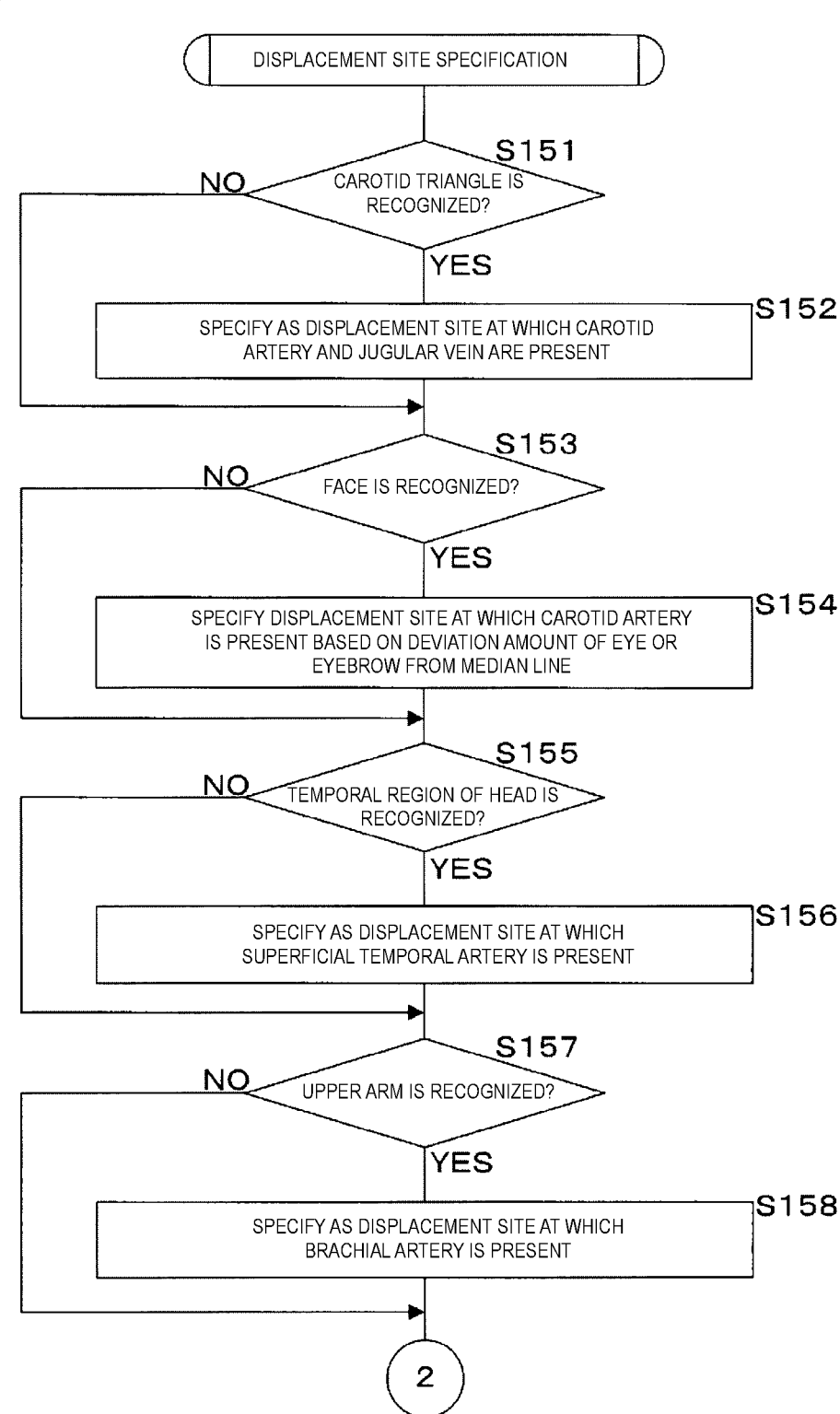
FIG. 8 is a flowchart illustrating a processing procedure of specifying displacement sites.
Figure 9:
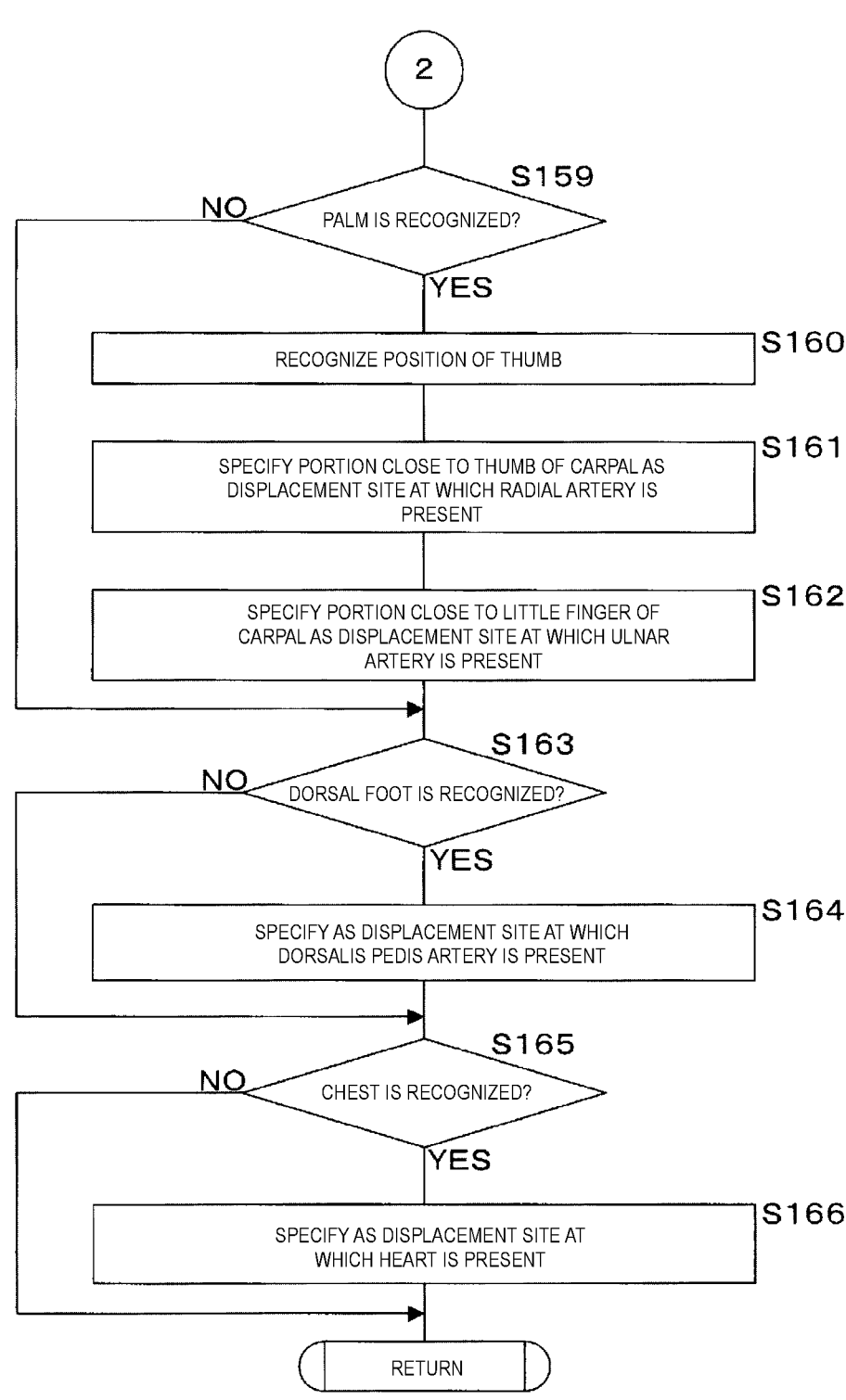
FIG. 9 is a flowchart illustrating the processing procedure of specifying the displacement sites.

FIGS. 8 and 9 are flowcharts illustrating a processing procedure of specifying the displacement sites. The processing unit 11 determines whether a region of the carotid triangle is recognized by the processing in S113 (S151). When the region of the carotid triangle is recognized (S151: YES), the processing unit 11 specifies the region as a displacement site at which the carotid artery and a jugular vein are present (S152).

When the processing in S152 is ended or when it is determined in S151 that the region of the carotid triangle is not recognized (S151: NO), the processing unit 11 determines whether the face of the user is recognized by the processing in S113 (S153). When it is determined that the face of the user is recognized (S153: YES), the processing unit 11 detects any one of a contour, an eye, an eyebrow, a nose, a mouth, a nasolabial fold, an ear, and a chin of the face, and specifies a displacement site at which the carotid artery is present based on a deviation amount of each part such as the eye from a median line (S154). The processing unit 11 detects the contour, the eye, the eyebrow, the nose, the mouth, the nasolabial fold, the ear, or the chin of the face, for example, by using the learning model 19. In addition, an image portion of the face in the infrared image may be extracted, and the eye and the like of the face may be detected based on a rule base by binarization, pattern matching processing, or the like. On the other hand, since the processing unit 11 can recognize left and right parts of the human body, for example, the right chest and the left chest, and the right upper arm and the left upper arm by the processing in S113, a straight line that divides the left and right parts can be specified as the median line. From a positional relationship between the median line and the left and right parts such as the eyes, whether the face is facing a right side or a left side, a rotation angle of the neck, or the like can be estimated. When the face is facing the right side, a left side of the neck recognized by the learning model 19 may be specified as the displacement site at which the carotid artery is present. When the face is facing the left side, a right side of the neck may be specified as the displacement site at which the carotid artery is present. In addition, the displacement site may be specified by being further narrowed down from a part corresponding to the right carotid artery or the left carotid artery according to a rotation amount of the neck.

When the processing in S154 is ended or when it is determined in S153 that the face is not recognized (S153: NO), the processing unit 11 determines whether the temporal region of the head of the user is recognized by the processing in S113 (S155). When it is determined that the temporal region of the head is recognized (S155: YES), the processing unit 11 specifies a measurement unit as a displacement site at which the superficial temporal artery is present (S156).

When the processing in S156 is ended or when it is determined in S155 that the temporal region of the head is not recognized (S155: NO), the processing unit 11 determines whether the upper arm is recognized by the processing in S113 (S157). When it is determined that the upper arm is recognized (S157: YES), the processing unit 11 specifies the upper arm as a displacement site at which the brachial artery is present (S158).

When the processing in S158 is ended or when it is determined in S157 that the upper arm is not recognized (S157: NO), the processing unit 11 determines whether the palm is recognized by the processing in S113 (S159). When it is determined that the palm is recognized (S159: YES), the processing unit 11 recognizes a position of the thumb from an image portion of the palm (S160), and specifies the portion close to the thumb of the carpal recognized by the processing in S113 as a displacement site at which the radial artery is present (S161). In addition, the processing unit 11 specifies the portion close to the little finger of the carpal recognized by the processing in S113 as a displacement site at which the ulnar artery is present (S162).

When the palm is recognized, that is, when the palm is facing the infrared sensor 13, the learning model 19 recognizes the inside of the carpal as the carpal. The inside of the carpal is a site at which the surface of the living body is displaced due to the pulse of the radial artery and the ulnar artery. When the dorsum manus is facing the infrared sensor 13, the learning model 19 recognizes an outside of the carpal as the carpal.

In addition, when the learning model 19 performs machine learning so as to distinguish and recognize a thumb side on the inside of the carpal, a little finger side on the inside of the carpal, and the outer side of the carpal, recognition processing of the orientation of the palm and the position of the thumb is not necessary. The learning model 19 can directly recognize the displacement site at which the radial artery is present and the displacement site at which the ulnar artery is present.

When the processing in S162 is ended or when it is determined in S159 that the palm is not recognized (S159: NO), the processing unit 11 determines whether the dorsal foot is recognized by the processing in S113 (S163). When it is determined that the dorsal foot is recognized (S163: YES), the processing unit 11 specifies the dorsal foot as a displacement site at which the dorsalis pedis artery is present (S164).

When the processing in S164 is ended or when it is determined in S163 that the dorsal foot is not recognized (S163: NO), the processing unit 11 determines whether the chest is recognized by the processing in S113 (S165). When it is determined that the chest is not recognized (S165: NO), the processing unit 11 ends the processing of specifying the displacement sites. When it is determined that the chest is recognized (S165: YES), the processing unit 11 specifies the chest as a displacement site at which the heart is present (S166), and ends the processing of specifying the displacement sites.

According to the above processing, the displacement sites can be specified at each of which vibration or the pulse of the blood vessel is propagated and the surface of the living body is displaced. Specifically, the processing unit 11 can specify the displacement sites at which the surface of the living body is displaced by the pulse of the carotid artery, the temporal artery, the brachial artery, the radial artery, the ulnar artery, the dorsalis pedis artery, and the heart. In addition, the processing unit 11 can specify a site at which the jugular vein is present.

Figure 10:
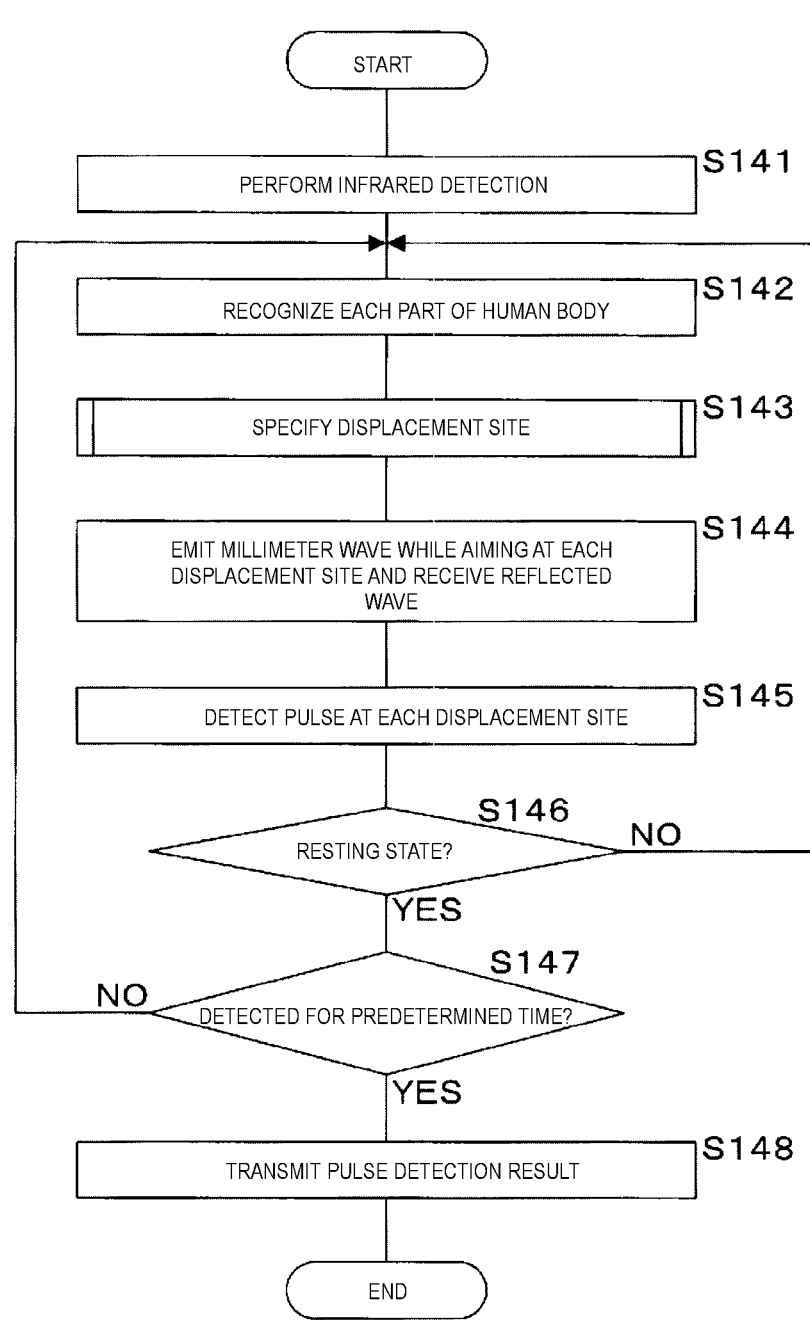
FIG. 10 is a flowchart illustrating a processing procedure of the sensor device according to Embodiment 1.

FIG. 10 is a flowchart illustrating a processing procedure of the sensor device 9 according to Embodiment 1. When the processing unit 91 of the sensor device 9 receives the detection instruction transmitted from the information processing device 1, the processing unit 91 executes the following processing. The processing unit 91 performs infrared detection on the user by using the infrared sensor 93 (S141). Specifically, when the infrared sensor 93 is an infrared camera, the processing unit 91 images the user by using the infrared camera and acquires the infrared image data of the user. When the infrared sensor 93 is a LiDAR, the processing unit 91 acquires the point group data of the user by using the LiDAR. The processing unit 91 converts the point group data into the two-dimensional infrared image data.

Next, the processing unit 91 inputs the infrared image data to the learning model 99 to recognize each part of the human body of the user in the infrared image (S142). Then, the processing unit 91 specifies the displacement sites at each of which the surface of the living body is periodically displaced due to the pulse of the heart or the blood vessel (S143). Details of the processing of specifying the displacement sites are the same as the processing of specifying the displacement sites by the information processing device 1. The processing unit 91 that executes the processing in S143 functions as a second specifying unit that specifies the displacement sites at each of which the surface of the living body is displaced due to the heart or the blood vessel.

Next, based on a specification result in S143, the processing unit 91 sequentially emits millimeter waves while aiming at each specified displacement site, receives reflected waves (S144), and detects the pulse of the heart or blood vessel at each displacement site (S145).

The processing unit 91 that executes the processing in S144 to S145 functions as the detection unit that detects the pulse of the heart or the blood vessel based on the displacement of the surface of the living body at the specified displacement site.

Next, the processing unit 91 determines whether the user is in a resting state based on a period of the detected pulse (S146).

When it is determined that the user is not in the resting state (S146: NO), the processing unit 91 returns the processing to S142. When it is determined that the user is in the stable state (S146: YES), the processing unit 91 determines whether the pulse of each displacement site is detected for a predetermined time (S147). The predetermined time can be, for example, a time that is several times an average pulse period of the heart and the blood vessel. When it is determined that the pulse is detected for a time shorter than the predetermined time (S147: NO), the processing unit 91 returns the processing to S142. When it is determined that the pulse is detected for the predetermined time or longer than the predetermined time (S147: YES), the processing unit 91 transmits information of the pulse detection result to the information processing device 1 (S148), and ends the processing.

Figure 11:
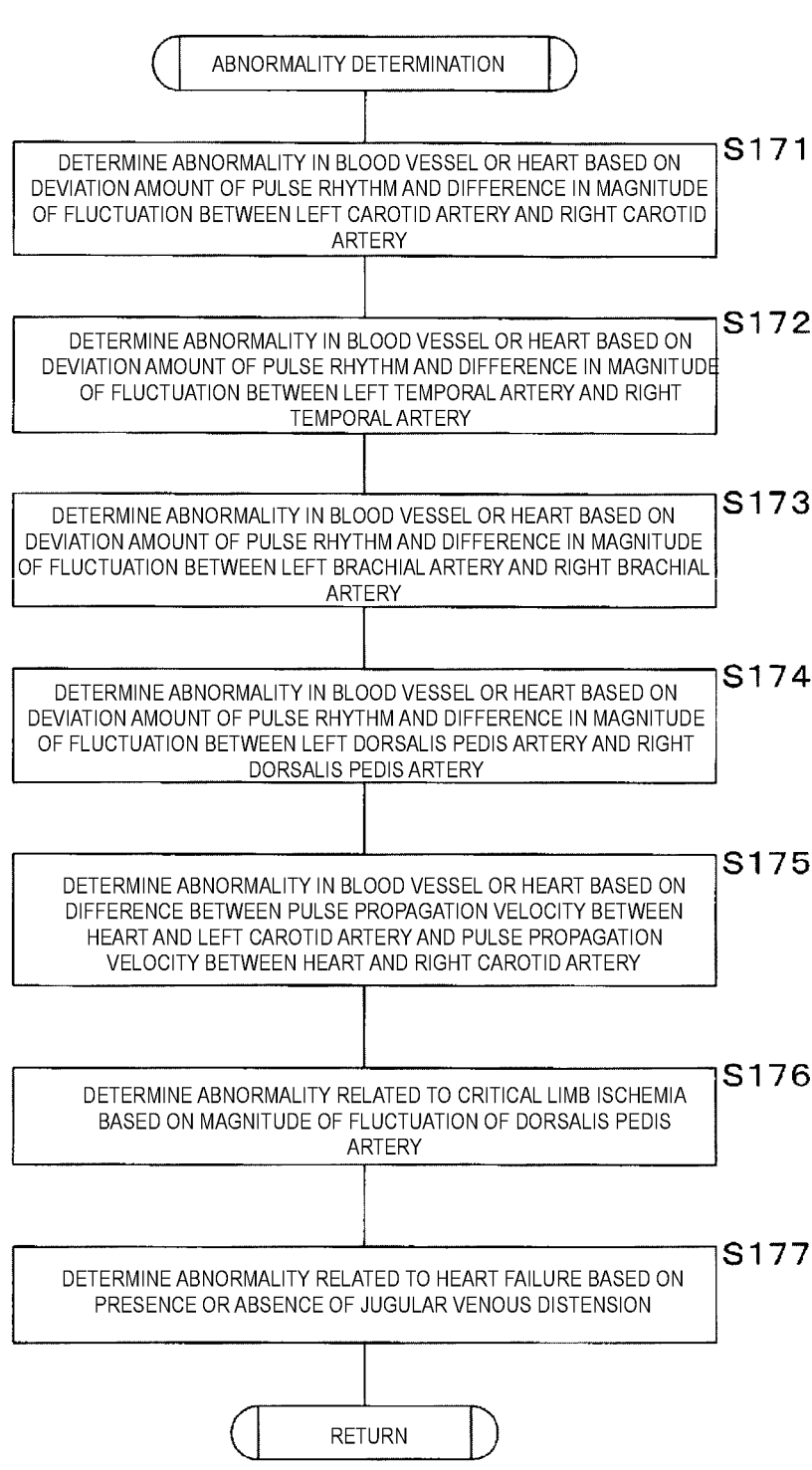
FIG. 11 is a flowchart illustrating an abnormality determination processing procedure.

FIG. 11 is a flowchart illustrating an abnormality determination processing procedure. The processing unit 11 determines an abnormality in the blood vessel or the heart based on a deviation amount of the pulse rhythm and a difference in magnitude of the fluctuation between the left carotid artery and the right carotid artery (S171). When the deviation amount of the pulse rhythm is equal to or greater than a predetermined threshold, the processing unit 11 determines the abnormality in the blood vessel or the heart. In other words, when a time difference between the peak time point of the pulse at the first displacement site and the peak time point of the pulse at the second displacement site is equal to or greater than a predetermined threshold, the processing unit 11 determines the abnormality in the blood vessel or the heart. Similarly, when the difference in magnitude of the fluctuation is equal to or greater than a predetermined threshold, the processing unit 11 determines the abnormality in the blood vessel or the heart. When the deviation amount of the pulse rhythm and the difference in magnitude of the fluctuation of the pulse are relatively large, abnormalities such as arteriosclerosis and stenosis of the blood vessel can be suspected. For example, the processing unit 11 determines an ischemic and hemorrhagic cerebral vascular abnormality. That is, the processing unit 11 determines an abnormality related to stroke, cerebral infarction, and cerebral hemorrhage. The same applies to the following.

Next, the processing unit 11 determines the abnormality in the blood vessel or the heart based on a deviation amount of the pulse rhythm and a difference in magnitude of the fluctuation between a left temporal artery and a right temporal artery (S172). For example, the processing unit 11 determines the ischemic and hemorrhagic cerebral vascular abnormality. That is, the processing unit 11 determines the abnormality related to stroke, cerebral infarction, and cerebral hemorrhage.

The processing unit 11 determines the abnormality in the blood vessel or the heart based on a deviation amount of the pulse rhythm and a difference in magnitude of the fluctuation between a left brachial artery and a right brachial artery (S173).

The processing unit 11 determines the abnormality in the blood vessel or the heart based on a deviation amount of the pulse rhythm and a difference in magnitude of the fluctuation between a left dorsalis pedis artery and a right dorsalis pedis artery (S174). For example, the processing unit 11 determines an abnormality in a blood vessel of the foot.

Next, the processing unit 11 determines the abnormality in the blood vessel or the heart based on a difference between a pulse propagation velocity between the heart and the left carotid artery and a pulse propagation velocity between the heart and the right carotid artery (S175). When the difference between the propagation velocities is equal to or greater than a predetermined threshold, some abnormalities in the heart or the blood vessel can be suspected. For example, the processing unit 11 determines the ischemic and hemorrhagic cerebral vascular abnormality. That is, the processing unit 11 determines the abnormality related to stroke, cerebral infarction, and cerebral hemorrhage.

Next, the processing unit 11 determines an abnormality related to the critical limb ischemia based on a magnitude of a fluctuation of a pulse of the dorsalis pedis artery (S176). When the fluctuation of the pulse of the dorsalis pedis artery is less than a predetermined threshold, the processing unit 11 can determine that there is a critical limb ischemia abnormality.

Next, the processing unit 11 analyzes infrared image data in the region of the carotid triangle and analyzes point group data in the region of the carotid triangle, thereby executing processing of detecting jugular venous distension, and determining an abnormality related to heart failure based on presence or absence of the jugular venous distension (S177).

In the above description, the example in which the abnormality in the heart or the blood vessel can be determined based on the deviation amount of the pulse rhythm and the difference in magnitude of the fluctuation between the left and right arteries has been described, but the abnormality in the heart or the blood vessel may be determined based on a deviation amount of the temporal change of the pulse, the pulse rate, the heartbeat, the pulse rhythm, or the peak time point of the pulse, or a difference in magnitude of the fluctuation between any two of the pulse of the carotid artery, the pulse of the superficial temporal artery, the pulse of the brachial artery, the pulse of the radial artery, the pulse of the ulnar artery, the pulse of the dorsalis pedis artery, and the heartbeat. Regarding the presence or absence of the jugular venous distension, the abnormality related to heart failure may be determined based on a size and a shape of swelling of the jugular vein. Further, the presence or absence of the jugular venous distension and the abnormality related to heart failure based on the presence or absence of the jugular venous distention may be determined by comparing the magnitude of the fluctuation of the pulse or the heartbeat of the above artery, or the like.

In the above description, the abnormality determination is performed based on the current pulses of the heart and the blood vessel, but the abnormality in the heart or the blood vessel may be determined by comparing the information on the past pulse of the user stored in the user DB 18 with the information on the current pulse. For example, the processing unit 11 may determine an increase or decrease in the heartbeats of the user as the abnormality in the heart or the blood vessel. Further, the information related to the past pulse detected in an environment similar to the current environment may be compared with the information related to the current pulse. The abnormality in the heart or the blood vessel can be determined more accurately.

Figure 12:
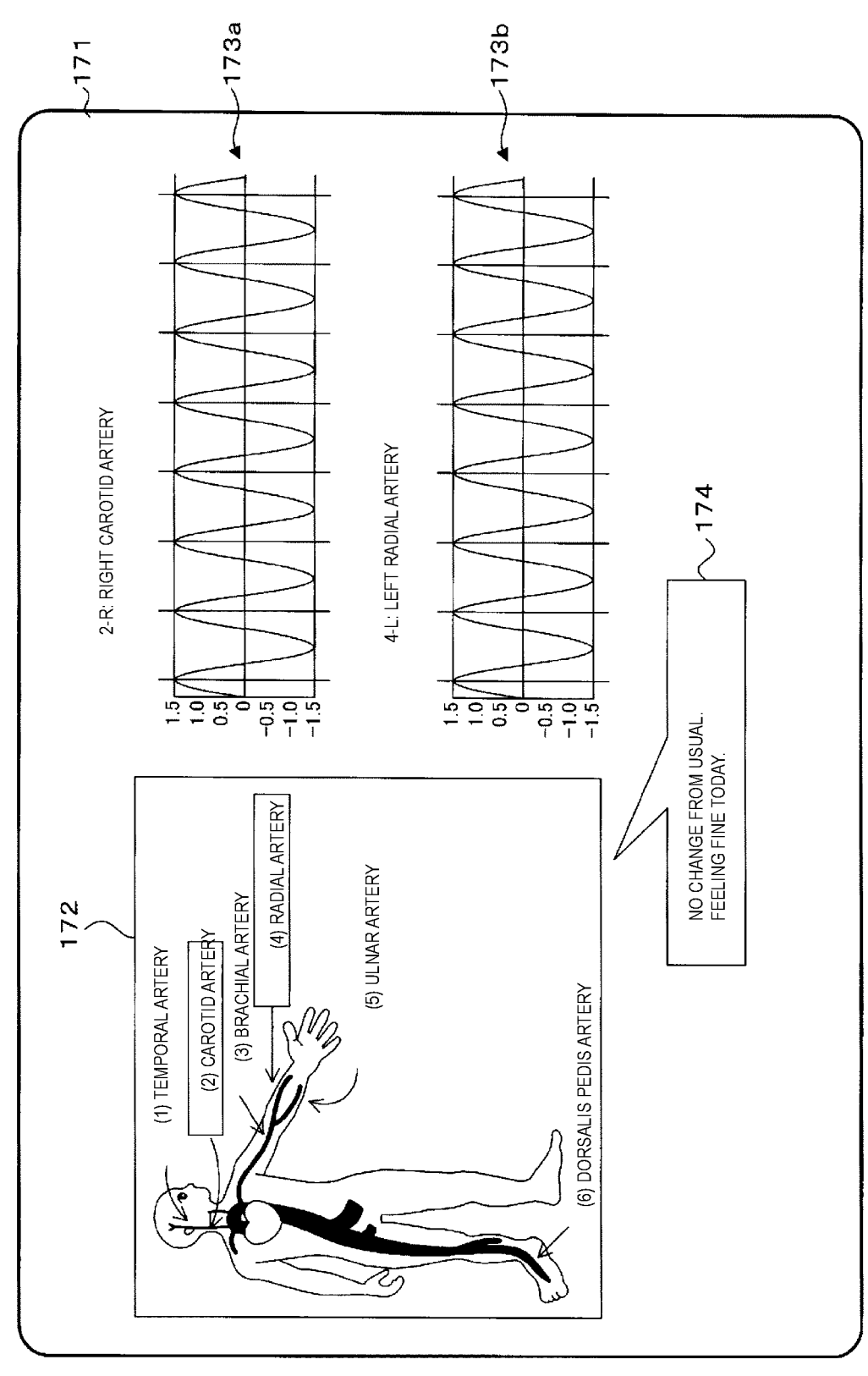
FIG. 12 is a schematic diagram illustrating an example of a determination result display image.
Figure 13:
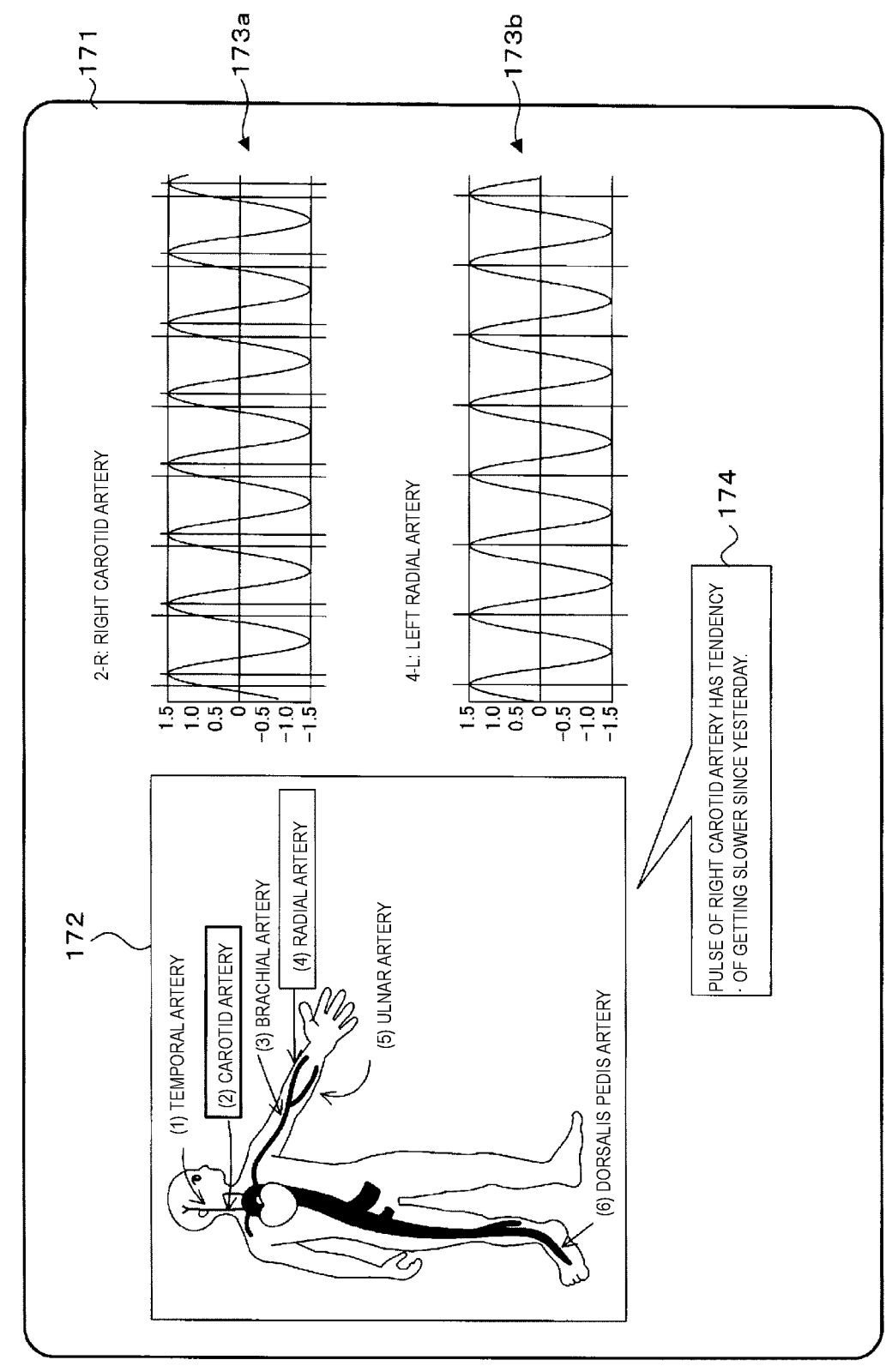
FIG. 13 is a schematic diagram illustrating an example of the determination result display image.
Figure 14:
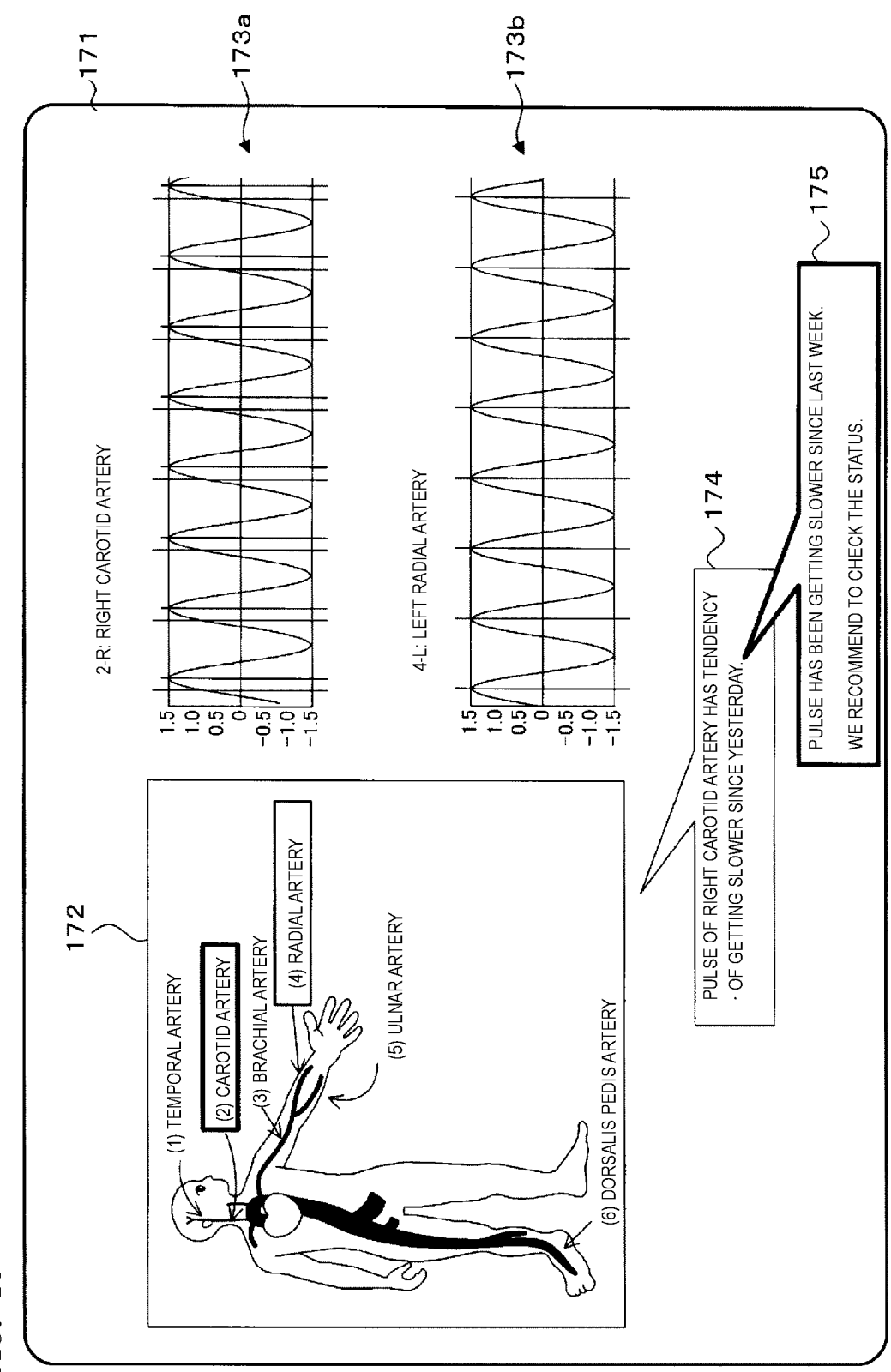
FIG. 14 is a schematic diagram illustrating an example of the determination result display image.

FIGS. 12, 13, and 14 are schematic diagrams illustrating examples of the determination result display image 171. The processing unit 11 generates the determination result display image 171 as illustrated in FIGS. 12 to 14 by the processing in S125 and S127. On the determination result display image 171, for example, a human body image 172 is displayed in which a human body and various arteries and the heart to be detected are drawn. The human body image 172 includes character images "(1) Temporal artery", "(2) Carotid artery", "(3) Brachial artery", "(4) Radial artery", "(5) Ulnar artery", and "(6) Dorsalis pedis artery" indicating names of various arteries.

The processing unit 11 may display a character image corresponding to an artery whose pulse can be detected and a character image corresponding to an artery whose pulse cannot be detected in different forms. For example, the processing unit 11 may highlight the character image corresponding to the artery whose pulse can be detected and display the character image corresponding to an artery whose pulse cannot be detected with tightly written characters.

The determination result display image 171 includes graphs 173a and 173b indicating temporal changes of the pulses of a plurality of arteries. In the examples illustrated in FIGS. 12 to 14, the two graphs 173a and 173b indicating temporal changes of the pulses of the carotid artery and the radial artery are displayed. In each of the graphs 173a and 173b, a state of the pulse may be displayed in real time or a state of the pulse in a certain period of time may be displayed statically.

The two graphs 173a and 173b indicating the pulse of each artery may be displayed at predetermined screen positions corresponding to each artery and the heart, or only the graphs 173a and 173b indicating the detected pulses of the arteries may be displayed. The processing unit 11 may receive selection of a graph to be displayed from the operation unit 16 and display the graphs 173a and 173b indicating the pulse of the selected artery. In addition, a peak of the pulse may be displayed as a zero point, for example, on the graphs 173a and 173b.

When the determination result is normal, the processing unit 11 may display the graphs 173a and 173b indicating pulse states of a representative one or more arteries, as illustrated in FIG. 12. For example, the graphs 173a and 173b indicating the pulse states of the carotid artery and the radial artery are displayed. In addition, the processing unit 11 may display a character image corresponding to an artery displayed in the graph in a different form from the other character images. For example, the processing unit 11 may highlight the character image.

When the determination result is abnormal, the processing unit 11 displays the graphs 173a and 173b indicating temporal changes of pulses of two arteries that are basis of the abnormality determination on the determination result dis-play image 171, as illustrated in FIGS. 13 and 14. In addition, the processing unit 11 may highlight a character image indicating the artery that is basis of the abnormality determination, in a different form from the normal state. For example, the processing unit 11 may highlight a character image indicating an artery detected at the time of the normal determination in green, and highlight an artery that is basis at the time of the abnormality determination in red.

Further, the determination result display image 171 includes a message image 174 indicating whether the determination result is normal, as illustrated in FIGS. 12 and 13.

Further, when the finding information of the medical personnel is received, the determination result display image 171 includes a finding message image 175 indicating the finding information, as illustrated in FIG. 14.

By the determination result display image 171 as illustrated in FIGS. 12 to 14, the user can know whether the pulse state of the heart and the blood vessel, and the heart or the blood vessel are normal. The determination result display image 171 may be transmitted to the first communication terminal 2 and the second communication terminal 3 as the determination result.

The determination result display image 171 is an example, and other information may be displayed. For example, a graph indicating the temporal change of the pulse of the heart or the blood vessel one day ago, one week ago, or one year ago may be compared with and displayed side by side or superimposed with the current graph. In addition, information such as the heartbeat and the pulse rate may be displayed.

As described above, according to the information processing system and the like according to Embodiment 1, the pulse of the heart or the blood vessel of the user can be detected and the abnormality in the heart or the blood vessel can be determined. Specifically, the processing unit 11 can determine the abnormality in the heart or the blood vessel, such as arteriosclerosis and stenosis, by comparing the pulse rate, the heartbeat, the pulse rhythm, the magnitude of the fluctuation of a pulse, and the like at the plurality of displacement sites. More specifically, the abnormality in the heart or the blood vessel can be determined based on the time difference in peak time point of the pulse and the difference in magnitude of the fluctuation of a pulse between the carotid artery and the radial artery or between a pair of the left and right arteries. In addition, the ischemic and hemorrhagic cerebral vascular abnormality can be determined based on the magnitudes of the fluctuations of a pulse of the temporal artery, the carotid artery, or the like. That is, the abnormality related to stroke, cerebral infarction, and cerebral hemorrhage can be determined. In addition, the presence or absence of the critical limb ischemia abnormality can be determined based on the magnitude of the fluctuation of a pulse in the dorsalis pedis artery. Further, the abnormality related to heart failure can be determined by detecting the jugular venous distension.

Since the displacement sites are specified by using the infrared sensor 13 and then the millimeter waves are emitted to the displacement sites, the pulses of the blood vessel and the heart at the displacement sites can be more accurately and efficiently detected. According to the infrared sensor 13, the displacement sites can be more efficiently specified as compared with a case of using the millimeter waves. On the other hand, according to the millimeter wave sensor 14, the pulse at the displacement site hidden by the clothing, which cannot be detected by the infrared sensor 13 can be detected. By compensating for the advantages and disadvantages of the infrared sensor 13 and the millimeter wave sensor 14 in this way, the pulses of the various arteries and the heart can be more accurately and efficiently detected, and the abnormality in the blood vessels and the heart can be determined.

Further, the information processing system can detect the pulses of the heart and the blood vessels by recognizing each part of the body of the user from two different directions and emitting the millimeter wave from the two directions, so that the abnormality in the heart or the blood vessel can be more efficiently detected.

Since the information processing device 1 emits the millimeter waves while aiming at the displacement sites specified by the infrared sensor 13 to detect the pulse, the pulse of the heart or each artery can be efficiently and accurately detected.

According to Embodiment 1, the determination result can be notified to the family member or the medical personnel. In addition, when there is an abnormality in the heart or the blood vessel and there is the finding information of the medical personnel, the information processing device 1 can display the finding information of the medical personnel on the display unit 17. In addition, the finding information of the medical personnel can be transmitted to the first communication terminal 2 of the family member. Therefore, after detecting the abnormality in the heart or the blood vessel at an early stage, the user and the family member can be notified of reliable information from the medical personnel.

In Embodiment 1, the example in which the infrared sensors 13 and 93 recognize each part of the human body of the user and the displacement sites has been described, but the infrared sensors 13 and 93 may be replaced by an imaging device that images the user with visible light. The processing unit 11 can similarly recognize each part of the human body based on image data of the user imaged by the visible light, and specify the displacement sites.

The example in which the pulse at each of the displacement sites of the human body is detected by using the millimeter wave sensors 14 and 94 has been described, but a sensor that transmits and receives electromagnetic waves in a terahertz band may be provided. By emitting the electromagnetic waves in the terahertz band to the displacement site and receiving the reflected waves from the displacement site, the pulse at the displacement site can be detected in the same manner as the millimeter wave sensors 14 and 94.

The information processing device 1 including the infrared sensors 13 and 93 and the millimeter wave sensors 14 and 94 has been described, but the infrared sensors 13 and 93 or the millimeter wave sensors 14 and 94 may be devices externally connected in a wired or wireless manner.

In Embodiment 1, the example in which the displacement sites and the pulses in the body of the user are detected by using the infrared sensors 13 and 93 and the millimeter wave sensors 14 and 94 in the horizontal direction and the vertical direction has been described, but the detection directions are examples, and the displacement sites and the pulses of the user may be detected from a direction oblique to a horizontal plane.

In Embodiment 1, the example in which the displacement sites and the pulses in the body of the user are detected by using the infrared sensors 13 and 93 and the millimeter wave sensors 14 and 94 from two directions has been described, but the detection directions are not limited to two directions, and the displacement sites may be specified and the pulses may be detected from three or more directions.

In Embodiment 1, the example in which a home computer executes the computer programs P1 and P2 according to Embodiment 1 has been described, and a cloud computer may execute the computer programs P1 and P2 according to Embodiment 1 to implement the information processing method. In addition, the computer programs P1 and P2 may be distributed and executed in a plurality of server computers.

In Embodiment 1, the information processing device 1 and the sensor device 9 share and execute the processing, but all or a part of the processing based on the computer program P1 may be executed by the sensor device 9, or all or a part of the processing based on the computer program P2 may be executed by the information processing device 1.

In Embodiment 1, a configuration in which the information processing device 1 includes the first specifying unit, the detection unit, and the determination unit, the sensor device 9 includes the second specifying unit and the detection unit has been described, but the arrangement of each unit is an example. The first specifying unit, the second specifying unit, the detection unit, and the determination unit may be appropriately provided in any one or both of the information processing device 1 and the sensor device 9.

Embodiment 2

An information processing system according to Embodiment 2 differs from Embodiment 1 in an information processing procedure. Other configurations of the information processing system are the same as those of the information processing system according to Embodiment 1, similar portions are denoted by the same reference numerals, and detailed description of similar portions denoted by the same reference numerals is omitted.

Figure 15:
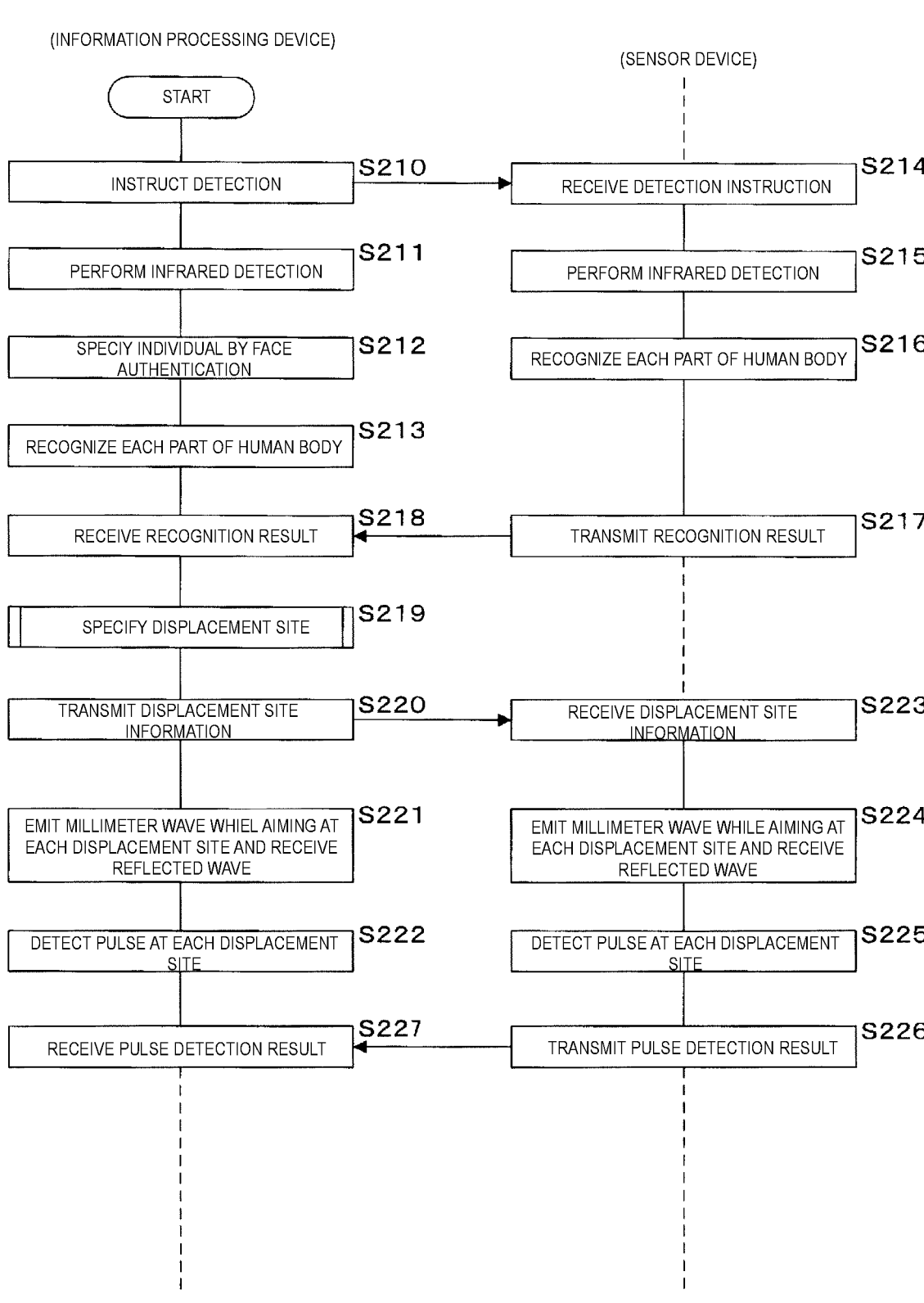
FIG. 15 is a flowchart illustrating an information processing procedure according to Embodiment 2.

FIG. 15 is a flowchart illustrating an information processing procedure according to Embodiment 2. The information processing device 1 executes the following processing at any timing. As in Embodiment 1, the processing unit 11 transmits, to the sensor device 9, an instruction signal to instruct processing of specifying displacement sites of a user and detecting a pulse (S210), performs infrared detection on the user by using the infrared sensor 13 (S211), specifies an individual by face authentication processing using a result of the infrared detection (S212), and inputs infrared image data to the learning model 19 to recognize each part of a human body of the user in an infrared image (S213). That is, the processing unit 11 recognizes each part of the human body of the user as viewed from a substantially horizontal direction. In other words, the processing unit 11 image-recognizes each part of the user in the infrared image obtained by detecting the human body from the substantially horizontal direction by using the infrared sensor 13.

The processing unit 91 of the sensor device 9 receives the instruction signal transmitted from the information processing device 1 (S214). The processing unit 91 that receives the instruction signal performs infrared detection on the user by using the infrared sensor 93 (S215), and inputs the infrared image data to the learning model 99 to recognize each part of the human body of the user in the infrared image (S216). That is, the processing unit 91 recognizes each part of the human body of the user as viewed from above. In other words, the processing unit 11 image-recognizes each part of the user in the infrared image obtained by detecting each part from substantially vertically above by using the infrared sensor 93.

Then, the processing unit 91 transmits information of a recognition result, obtained by the processing in S216, to the information processing device 1 via the communication unit 95 (S217).

The processing unit 11 of the information processing device 1 receives, via the communication unit 15, the information of the recognition result transmitted from the sensor device 9 (S218). Then, based on the recognition result for each part of the user obtained by the information processing device 1 and the recognition result for each part of the user obtained by the sensor device 9, the processing unit 11 specifies displacement sites at each of which a surface of a living body is periodically displaced due to a pulse of a heart or a blood vessel (S219).

The processing unit 11 may specify one displacement site by using only the recognition result obtained by the information processing device 1, or may specify one displacement site by using only the recognition result obtained by the sensor device 9. The method for specifying the displacement sites is the same as that in Embodiment 1.

For example, when the information processing device 1 cannot recognize the dorsal foot and the sensor device 9 can recognize the dorsal foot, the processing unit 11 specifies the dorsal foot recognized by the sensor device 9 as a displacement site at which a dorsal artery is present. In this case, the processing unit 11 temporarily stores information indicating that the device that can detect the pulse of the dorsal artery is the sensor device 9.

On the contrary, when the information processing device 1 can recognize the temporal region of the head and the sensor device 9 cannot recognize the temporal region of the head, the processing unit 11 specifies the temporal region of the head recognized by the information processing device 1 as a displacement site at which a superficial temporal artery is present. In this case, the processing unit 11 temporarily stores information indicating that the device that can detect a pulse of the superficial temporal artery is the information processing device 1.

In this way, when one of the information processing device 1 and the sensor device 9 can recognize a part corresponding to a displacement site at which an artery whose pulse is desired to be detected is present, the processing unit 11 can specify the part recognized by either the information processing device 1 or the sensor device 9 as the displacement site. The processing unit 11 temporarily stores information indicating the information processing device 1 or the sensor device 9 that can recognize the part as a device that can detect a pulse of the part.

For a part that can be recognized by both the information processing device 1 and the sensor device 9, the displacement site may be specified based on the recognition result of the information processing device 1. In addition, the displacement site may be specified by comparing a size of the part that can be recognized by the information processing device 1 and a size of the corresponding part that can be recognized by the sensor device 9 and using a recognition result of the device which can recognize the part with a relatively larger size.

The information processing device 1 may specify the displacement site by using both the recognition results of the information processing device 1 and the sensor device 9. For example, a displacement site at which a carotid artery is present can be recognized using both the recognition results. In S154 in Embodiment 1, a torsion amount of the neck is estimated based on the deviation amount of each part of the face from the median line, and the displacement site at which the carotid artery is present is specified, whereas in Embodiment 2, the torsion amount of the neck can be directly estimated based on recognition results of the head or the ear and the shoulder or the chest of the user recognized by the sensor device 9, and a displacement site at the neck recognized by the information processing device 1 can be specified based on the torsion amount.

Here, an example of the method for recognizing the displacement site at which the carotid artery is present is described, and the displacement site may be specified by appropriately combining the recognition results of the information processing device 1 and the sensor device 9.

After ending the processing in S219, the processing unit 11 transmits information, indicating the displacement site at which the sensor device 9 needs to detect the pulse, to the sensor device 9 via the communication unit 15 (S220).

Then, based on a specification result in S219, the processing unit 11 sequentially emits millimeter waves while aiming at each displacement site specified as a part at which pulse is to be detected on the information processing device 1 side, receives reflected waves (S221), and detects a pulse of the heart or the blood vessel at each displacement site (S222).

The sensor device 9 receives information indicating the displacement sites via the communication unit 95 (S223). Based on the information, the sensor device 9 that receives the information sequentially emits millimeter waves while aiming at each displacement site specified as a part at which pulse is to be detected on the sensor device 9 side, receives reflected waves (S224), and detects a pulse of the heart or the blood vessel at each displacement site (S225). Then, the processing unit 91 transmits information of a pulse detection result indicating the detected pulse at each displacement site to the information processing device 1 via the communication unit 95 (S226).

The information processing device 1 receives, via the communication unit 15, the information of the pulse detection result transmitted from the sensor device 9 (S227). Hereinafter, processing similar to the processing in S121 to S131 described in Embodiment 1 may be performed to determine the abnormality in the heart and the blood vessels of the user and execute notification processing.

According to the information processing system and the like according to Embodiment 2, by using both the recognition result for each part of a body of the user obtained by the information processing device 1 and the recognition result for each part of the body of the user obtained by the sensor device 9, the displacement sites to be irradiated with the millimeter waves can be specified, the pulse at each displacement site can be detected, and the abnormality in the heart or the blood vessel of the user can be determined.

According to Embodiment 2, since the displacement site at which the pulse is to be detected on the information processing device 1 side and the displacement site at which the pulse is to be detected on the sensor device 9 side are specified, the pulse at each site can be efficiently detected. That is, since the information processing device 1 and the sensor device 9 recognize the displacement sites to be detected by the self-devices and selectively detect the pulses at the displacement sites, the pulse at each part can be efficiently detected.

Embodiment 3

An information processing system according to Embodiment 3 differs from Embodiment 1 in an information processing procedure. Other configurations of the information processing system are the same as those of the information processing system according to Embodiment 1, similar portions are denoted by the same reference numerals, and detailed description similar portions denoted by same reference numerals is omitted.

Each of the infrared sensor 13 and the infrared sensor 93 according to Embodiment 3 is a device that can three-dimensionally detect a surface of a living body and a surface of clothing of a user, for example, an infrared laser such as a LiDAR. In addition, it is assumed that the information processing device 1 three-dimensionally recognizes each part of the body of the user using three-dimensional information, that is, point group data or voxel data.

Figure 16:
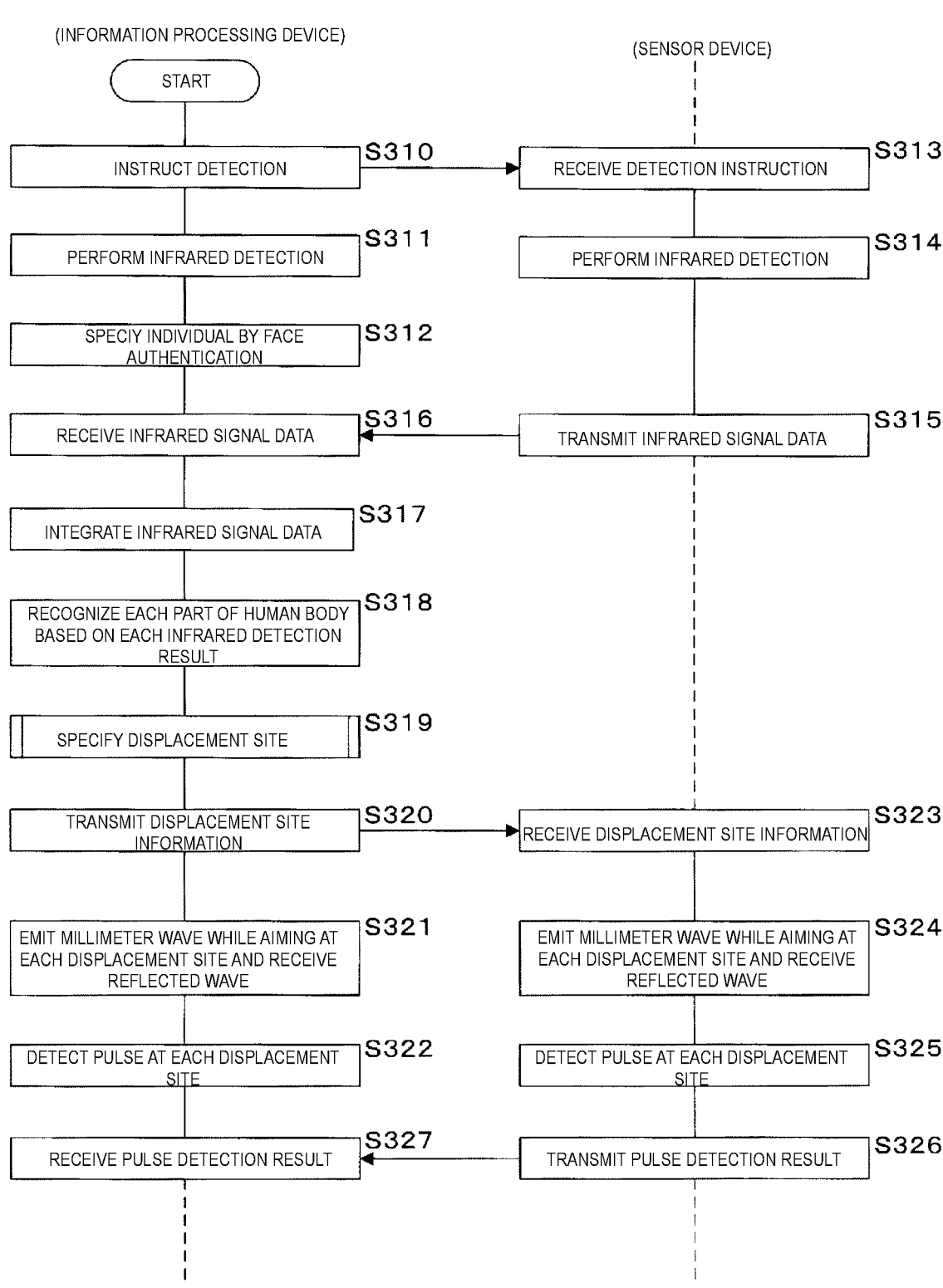
FIG. 16 is a flowchart illustrating an information processing procedure according to Embodiment 3.

FIG. 16 is a flowchart illustrating an information processing procedure according to Embodiment 3. The information processing device 1 executes the following processing at any timing. As in Embodiments 1 and 2, the processing unit 11 transmits, to the sensor device 9, an instruction signal to instruct processing of specifying displacement sites of the user and detecting a pulse (S310), performs infrared detection on the user by using the infrared sensor 13 (S311), and specifies an individual by face authentication processing using a result of the infrared detection (S312).

The processing unit 91 of the sensor device 9 receives the instruction signal transmitted from the information processing device 1 (S313). The processing unit 91 that receives the instruction signal performs infrared detection on the user by using the infrared sensor 93 (S314), and transmits infrared signal data output from the infrared sensor 93 to the information processing device 1 via the communication unit 95 (S315). The infrared signal data can be, for example, the point group data, which is three-dimensional information of the user.

The processing unit 11 of the information processing device 1 receives, via the communication unit 15, the infrared signal data transmitted from the sensor device 9 (S316). Then, the processing unit 11 integrates the infrared signal data output from the infrared sensor 13 and the infrared signal data received in S316 (S317).

In the point group data obtained by the infrared sensor 13, positions of many points on the surface of the living body or the surface of the clothing of the user are represented in three-dimensional coordinates in a coordinate system based on a position of the infrared sensor 13. In the point group data obtained by the infrared sensor 93, positions of many points on the surface of the living body or the surface of the clothing of the user are represented in three-dimensional coordinates in a coordinate system based on a position of the infrared sensor 93. Although the point group data obtained by the infrared sensor 13 and the point group data obtained by the infrared sensor 93 are data represented in different coordinate systems, if coordinate transformation is performed so as to match a plurality of points detected by both the infrared sensors 13 and 93, each point group data can be integrated, and more detailed three-dimensional information of the surface of the living body or the surface of the clothing of the user can be obtained.

Then, the processing unit 11 recognizes each part of the human body of the user by using the point group data obtained in S317 (S318). In S318, the processing unit 11 may recognize each part of the body of the user two-dimensionally or three-dimensionally. The processing unit 11 can recognize each part of the body of the user by converting, for example, the point group data into three-dimensional voxel data or two-dimensional infrared images and inputting the converted voxel data or infrared image to the learning model 19. The two-dimensional infrared images are an image obtained when the user is detected in a substantially horizontal direction by using the infrared sensor 13 and an image obtained when the user is detected in a substantially vertical direction by using the infrared sensor 93.

Next, the processing unit 11 specifies displacement sites at each of which the surface of the living body is periodically displaced due to a pulse of a heart or a blood vessel based on the recognition result for each part of the user obtained by the information processing device 1 (S319).

Hereinafter, the processing unit 11 may perform processing as in S220 to S227 in Embodiment 2 or S121 to S131 described in Embodiment 1 to determine the abnormality in the heart and the blood vessels of the user and execute notification processing.

According to the information processing system and the like according to Embodiment 3, the infrared signal data output from the infrared sensor 13 and the infrared sensor 93 are integrated to recognize each part of the body of the user, specify the displacement sites, and detect the pulse at each displacement site, so that the abnormality in the heart or the blood vessel of the user can be determined more accurately.

The pulse of the surface of the living body at each of the displacement sites may be three-dimensionally detected by using information on the displacement sites detected and three-dimensionally recognized by using the infrared sensor 13 and the infrared sensor 93, a detection result obtained by the millimeter wave sensor 14, and a detection result obtained by the millimeter wave sensor 94. The pulse of the heart or the blood vessel at each of the displacement sites can be detected more accurately.

Embodiment 4

The information processing device 1 according to Embodiment 4 is different from Embodiments 1 to 3 in that body motion and a pulse of a user are detected by using an acceleration sensor 5 and a contact sensor 6. Other configurations of the information processing device 1 are the same as those of the information processing device 1 according to Embodiments 1 to 3, similar portions are denoted by the same reference numerals, and detailed description of the similar portion denoted by the same reference numerals is omitted.

Figure 17:
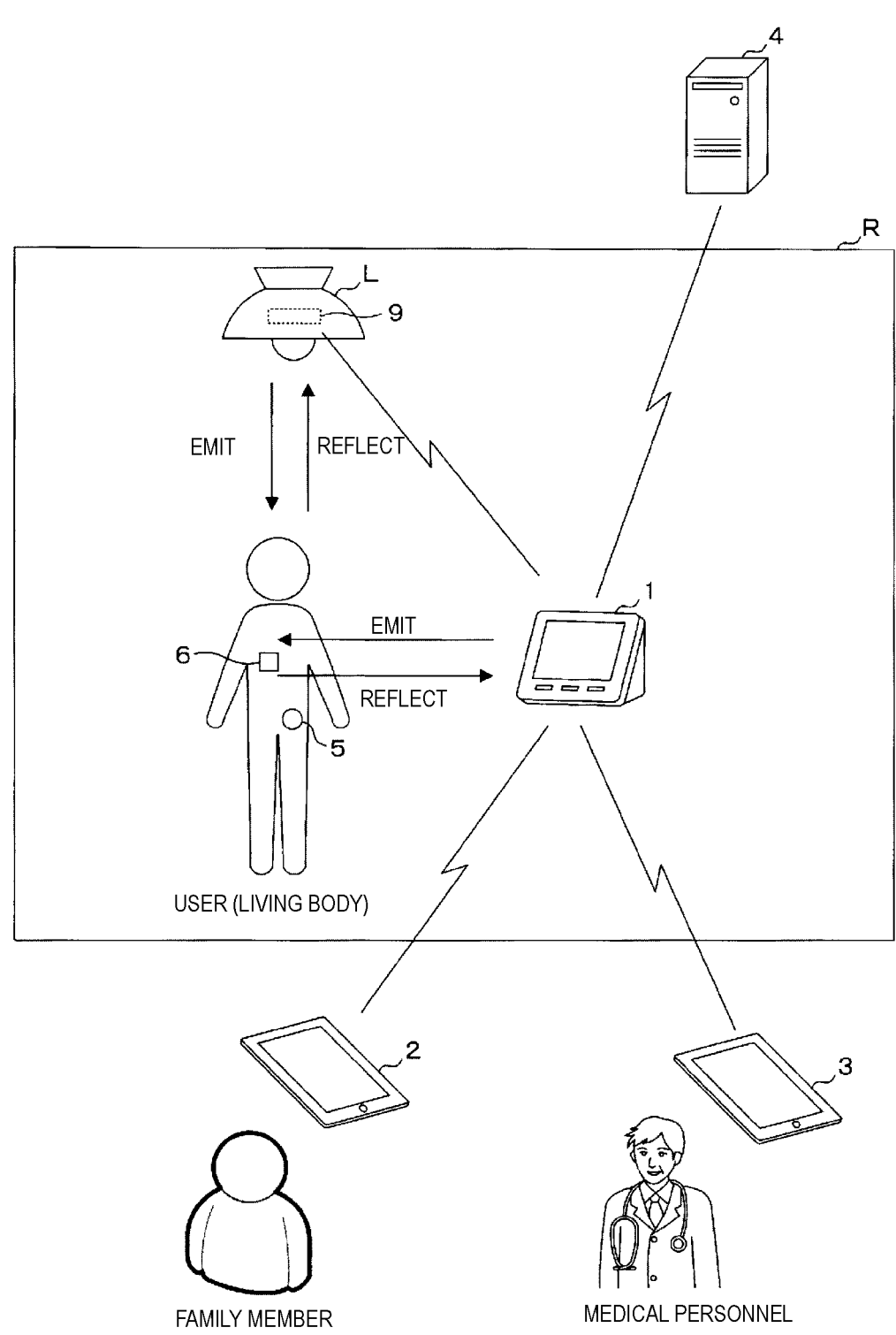
FIG. 17 is a diagram illustrating a configuration example of an information processing system according to Embodiment 4.

FIG. 17 is a diagram illustrating a configuration example of an information processing system according to Embodiment 4. The information processing system according to Embodiment 4 includes the information processing device 1 as in Embodiments 1 to 3, and further includes the acceleration sensor 5 attached to the user and the contact sensor 6 that detects a pulse of a heart or a blood vessel. The acceleration sensor 5 transmits acceleration signal data indicating an acceleration corresponding to movement of a body of the user to the information processing device 1. The contact sensor 6 is attached to a site at which a surface of a living body is displaced due to the pulse of the heart or the blood vessel, and transmits pulse signal data indicating the pulse to the information processing device 1. The contact sensor 6 may be attached to a site less likely to be irradiated with millimeter waves from the information processing device 1.

Figure 18:
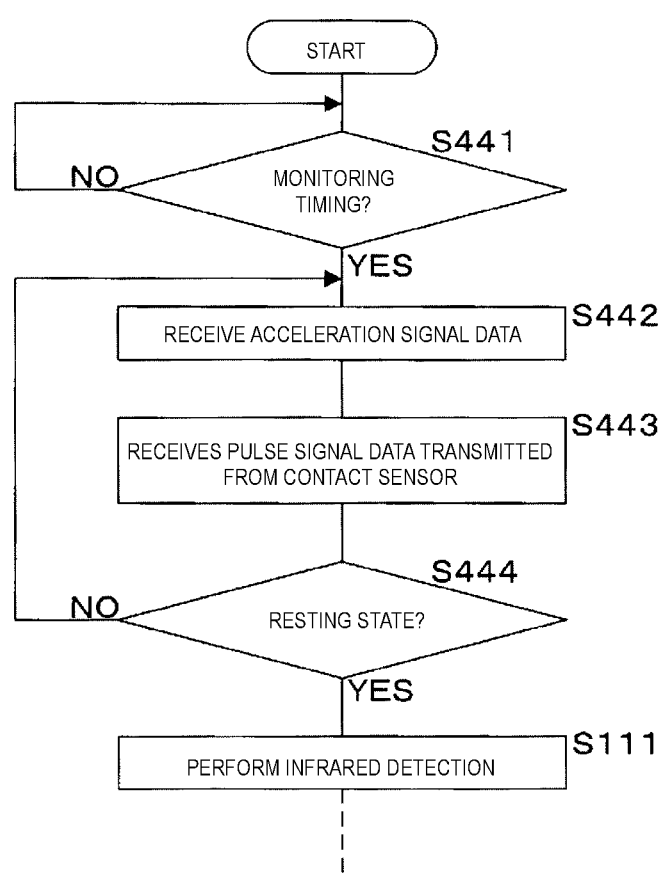
FIG. 18 is a flowchart illustrating an information processing procedure according to Embodiment 4.

FIG. 18 is a flowchart illustrating an information processing procedure according to Embodiment 4. The processing unit 11 of the information processing device 1 determines whether a current time is a predetermined monitoring timing (S441). The predetermined monitoring timing is any timing, and can be appropriately set by the user. When it is determined that the timing is not the monitoring timing (S441: NO), the processing unit 11 returns the processing to S441 and waits.

When it is determined that the current time is the monitoring timing (S441: YES), the processing unit 11 receives the acceleration signal data transmitted from the acceleration sensor 5 (S442), and receives the pulse signal data transmitted from the contact sensor 6 (S443).

Next, the processing unit 11 determines whether the user is in a resting state by determining whether a magnitude of body motion is less than a predetermined value based on the acceleration signal data (S444). When it is determined that the magnitude of the body motion is equal to or greater than the predetermined value and the user is not in the resting state (S444: NO), the processing unit 11 returns the processing to S442.

When it is determined that the magnitude of the body motion is less than the predetermined value and the user is in the resting state (S444: YES), the processing unit 11 specifies the displacement sites, detects the pulse of the heart and the blood vessels, and executes abnormality determination processing on the heart and the blood vessels, in the same processing procedure as in Embodiments 1 to 3. However, the processing unit 11 according to Embodiment 4 determines the abnormality in the heart or the blood vessel by using the pulse detected by using the millimeter wave sensor 14, which is a non-contact sensor, and the pulse indicated by the pulse signal data transmitted from the contact sensor 6.

As described above, according to the information processing system and the like according to Embodiment 4, by attaching the contact sensor 6 to a place less likely to be irradiated with the millimeter wave sensor 14, the abnormality in the heart or the blood vessel can be detected based on pulses of arteries at more sites. For example, a pulse of an axillary artery can be detected by attaching the contact sensor 6 under an armpit. In addition, pulses of a femoral artery, a popliteal artery, a posterior tibial artery, or the like can be detected by attaching the contact sensor 6 to a base of a thigh, a back of a knee, and a back of a medial malleolus, and the abnormality in the heart or the blood vessel can be determined more accurately.

Since the specifying of the displacement sites and the detection of the pulses are performed after confirming the resting state of the user by using the acceleration sensor 5, the abnormality determination processing can be efficiently performed.

The detailed description above describes embodiments of a computer program, an information processing method, an information processing device, and an information processing system. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A non-transitory computer-readable medium storing a computer program when executed by a computer determines an abnormality in a heart or a blood vessel of a living body by executing a process comprising:

specifying a first displacement site at which a surface of the living body is displaced due to a pulse of the heart or the blood vessel and wherein the first displacement site is detectable from a first direction, and wherein the first displacement site is specified based on signal data output from a first infrared sensor or visible light sensor facing the first direction with respect to the living body;

specifying a second displacement site at which the surface of the living body is displaced due to the pulse of the heart or the blood vessel and wherein the second displacement site is detectable from a second direction, and wherein the second displacement site is specified based on signal data output from a second infrared sensor or visible light sensor facing the second direction with respect to the living body;

detecting the pulse of the heart or the blood vessel based on the displacement of the surface of the living body at each of the specified first and second displacement sites;

determining an abnormality in the heart or the blood vessel based on information related to the detected pulse of the heart or the blood vessel, as detected by the first and second infrared sensors or visible light sensors at the first and second displacement sites; and outputting a determination result for the abnormality of the heart or the blood vessel of the living body on a display unit and highlighting a character image indicating an artery that is a basis of the abnormality determination, in a different form from a normal state on the display unit.

2. The non-transitory computer-readable medium according to claim 1, further comprising:

determining the abnormality in the heart or the blood vessel by comparing a pulse rate, a pulse rhythm, or a magnitude of a fluctuation of the pulse among the specified first and second displacement sites.

3. The non-transitory computer-readable medium according to claim 1, further comprising:

determining that there is the abnormality in the heart or the blood vessel when a time difference between a peak of the pulse at the first displacement site and a peak of the pulse at the second displacement site is equal to or greater than a threshold.

4. The non-transitory computer-readable medium according to claim 1, further comprising:

specifying the first and second displacement sites by infrared rays or visible light; and emitting millimeter waves or electromagnetic waves in a terahertz band and detecting the pulse of the heart or the blood vessel based on reflected waves from each of the first and second displacement sites of the living body.

5. The non-transitory computer-readable medium according to claim 1, further comprising:

specifying each of the first and second displacement sites based on signal data output from a first infrared sensor or visible light sensor facing the first direction with respect to the living body and signal data output from a second infrared sensor or visible light sensor facing the second direction with respect to the living body.

6. The non-transitory computer-readable medium according to claim 1, further comprising:

detecting the pulse of the heart or the blood vessel based on signal data output from a first millimeter wave sensor or terahertz band sensor that emits millimeter waves or electromagnetic waves in a terahertz band to the living body in the first direction and receives reflected waves from the first displacement site of the living body; and detecting the pulse of the heart or the blood vessel based on signal data output from a second millimeter wave sensor or terahertz band sensor that emits millimeter waves or electromagnetic waves in a terahertz band to the living body in the second direction and receives reflected waves from the second displacement site of the living body.

7. The non-transitory computer-readable medium according to claim 1, wherein the first direction is a substantially horizontal direction to the living body, and the second direction is a substantially vertical direction to the living body.

8. The non-transitory computer-readable medium to claim 1, further comprising:

emitting millimeter waves or electromagnetic waves in a terahertz band while aiming at the specified first and second displacement sites, and detecting the pulse of the heart or the blood vessel based on reflected waves from each of the first and second displacement sites.

9. The non-transitory computer-readable medium according to claim 1, further comprising:

detecting the pulse of the heart or the blood vessel at one of the first and second displacement sites based on signal data output from a contact sensor attached to the living body, and detecting the pulse of the heart or the blood vessel at another of the first and second displacement sites based on signal data output from a non-contact sensor.

10. The non-transitory computer-readable medium according to claim 1, further comprising:

determining whether a magnitude of body motion is less than a predetermined value based on signal data output from an acceleration sensor attached to the living body, the magnitude of body motion being a determination if the living body is in a resting state; and detecting the pulse of the heart or the blood vessel based on the displacement of the surface of the living body at each of the specified first and second displacement sites when the magnitude of body motion is less than the predetermined value.

11. The non-transitory computer-readable medium according to claim 1, further comprising:

specifying a region of a carotid triangle as the first displacement site;

detecting jugular venous distension; and determining an abnormality related to heart failure.

12. An information processing method for determining an abnormality in a heart or a blood vessel of a living body, the method comprising:

specifying a first displacement site at which a surface of the living body is displaced due to a pulse of the heart or the blood vessel and wherein the first displacement site is detectable from a first direction, and wherein the first displacement site is specified based on signal data output from a first infrared sensor or visible light sensor facing the first direction with respect to the living body;

specifying a second displacement site at which the surface of the living body is displaced due to the pulse of the heart or the blood vessel and wherein the second displacement site is detectable from a second direction, and wherein the second displacement site is specified based on signal data output from a second infrared sensor or visible light sensor facing the second direction with respect to the living body;

detecting the pulse of the heart or the blood vessel based on the displacement of the surface of the living body at each of the specified first and second displacement sites;

determining an abnormality in the heart or the blood vessel based on information related to the detected pulse of the heart or the blood vessel, as detected by the first and second infrared sensors or visible light sensors at the first and second displacement sites; and outputting a determination result for the abnormality of the heart or the blood vessel of the living body on a display unit and highlighting a character image indicating an artery that is a basis of the abnormality determination, in a different form from a normal state on the display unit.

13. The method according to claim 12, further comprising:

determining the abnormality in the heart or the blood vessel by comparing a pulse rate, a pulse rhythm, or a magnitude of a fluctuation of the pulse among the specified first and second displacement sites.

14. The method according to claim 12, further comprising:

determining that there is the abnormality in the heart or the blood vessel when a time difference between a peak of the pulse at the first displacement site and a peak of the pulse at the second displacement site is equal to or greater than a threshold.

15. The method according to claim 12, further comprising:

specifying each of the first and second displacement sites based on signal data output from a first infrared sensor or visible light sensor facing the first direction with respect to the living body and signal data output from a second infrared sensor or visible light sensor facing the second direction with respect to the living body.

16. The method according to claim 12, wherein the first direction is a substantially horizontal direction to the living body, and the second direction is a substantially vertical direction to the living body.

17. An information processing device for determining the abnormality in the heart or the blood vessel of the living body, the information processing device comprising a processor configured to execute the method according to claim 12.

18. An information processing system configured to determine an abnormality in a heart or a blood vessel of a living body, the information processing system comprising:

an information processing device including:

a first infrared sensor or visible light sensor configured to specify, from a first direction, a first displacement site at which a surface of the living body is displaced due to a pulse of the heart or the blood vessel; and a first millimeter wave sensor or terahertz band sensor configured to emit millimeter waves or electromagnetic waves in a terahertz band to the living body in the first direction and receive reflected waves from the displacement site of the living body;

a sensor device including:

a second infrared sensor or visible light sensor configured to specify, from a second direction, a second displacement site at which the surface of the living body is displaced due to the pulse of the heart or the blood vessel; and a second millimeter wave sensor or terahertz band sensor configured to emit millimeter waves or electromagnetic waves in a terahertz band to the living body in the second direction and receive reflected waves from the displacement site of the living body;

a processing unit configured to:

specify the first and second displacement sites respectively based on signal data output from the first infrared sensor or visible light sensor and the second infrared sensor or visible light sensor;

emit millimeter waves or electromagnetic waves in a terahertz band to the first and second displacement sites specified by the specifying unit from the first millimeter wave sensor or terahertz band sensor and the second millimeter wave sensor or terahertz band sensor, and to detect the pulse of the heart or the blood vessel based on the signal data output from the first millimeter wave sensor or terahertz band sensor and the second millimeter wave sensor or terahertz band sensor; and determine an abnormality in the heart or the blood vessel based on information related to the detected pulse of the heart or the blood vessel, as detected by the first and second infrared sensors or visible light sensors at the first and second displacement sites; and a display unit, which outputs a determination result for the abnormality of the heart or the blood vessel of the living body and highlights a character image indicating an artery that is a basis of the abnormality determination, in a different form from a normal state.

\* \* \* \* \*